United States Patent
Rau et al.

(10) Patent No.: US 10,617,351 B2
(45) Date of Patent: Apr. 14, 2020

(54) COGNITIVE BIOMETRIC SYSTEMS TO MONITOR EMOTIONS AND STRESS

(71) Applicant: Sackett Solutions & Innovations, LLC, Houston, TX (US)

(72) Inventors: Nemoy Rau, Houston, TX (US); Hans Rau, Noblesville, IN (US); Ramarao Inguva, Huntsville, AL (US); Visveshwar Baskaran, Houston, TX (US); Rick Story, Carmel, IN (US)

(73) Assignee: Sackett Solutions & Innovations LLC, Carmel, IN (US)

( * ) Notice: Subject to any disclaimer, the term of this patent is extended or adjusted under 35 U.S.C. 154(b) by 607 days.

(21) Appl. No.: 13/867,955

(22) Filed: Apr. 22, 2013

(65) Prior Publication Data

US 2013/0281798 A1    Oct. 24, 2013

Related U.S. Application Data

(60) Provisional application No. 61/637,259, filed on Apr. 23, 2012.

(51) Int. Cl.
*A61B 5/00* (2006.01)
*A61B 5/0205* (2006.01)
(Continued)

(52) U.S. Cl.
CPC ............ *A61B 5/4884* (2013.01); *A61B 3/113* (2013.01); *A61B 5/0476* (2013.01);
(Continued)

(58) Field of Classification Search
CPC ....... A61B 5/0002; A61B 5/021; A61B 5/024; A61B 5/026; A61B 5/16; A61B 5/164;
(Continued)

(56) References Cited

U.S. PATENT DOCUMENTS 6,186,145 B1 *  2/2001  Brown .................. A61B 19/00
                                                    128/897
6,625,485 B2 *  9/2003  Levendowski ........ A61B 5/048
                                                    128/920

(Continued)

FOREIGN PATENT DOCUMENTS

GB        2462449      2/2010
WO    WO2012108935    8/2012

OTHER PUBLICATIONS

Honda. K., et al., "Linear fuzzy clustering techniques with missing values and their application to local principal component analysis." Fuzzy Systems, IEEE Transactions on, Apr. 2004, pp. 183,193, vol. 12, No. 2.

(Continued)

*Primary Examiner* — Timothy J Neal
*Assistant Examiner* — William B Chou
(74) *Attorney, Agent, or Firm* — Hartman Global IP Law; Gary M. Hartman; Domenica N. S. Hartman

(57) ABSTRACT

The present invention provides methods and systems to periodically monitor the emotional state of a subject comprising the steps of: exposing the subject to a plurality of stimuli during a session; acquiring objective data from a plurality of monitoring sensors, wherein at least one sensor measures a physiological parameter; transferring the data to a database; and processing the data to extract objective information about the emotional state of the subject.

32 Claims, 17 Drawing Sheets

(51) Int. Cl.
| | |
|---|---|
| A61B 5/04 | (2006.01) |
| A61B 3/113 | (2006.01) |
| A61B 5/11 | (2006.01) |
| A61B 5/0476 | (2006.01) |
| A61B 5/0488 | (2006.01) |
| A61B 5/16 | (2006.01) |
| G16H 50/20 | (2018.01) |
| G06F 19/00 | (2018.01) |
| A61B 5/0402 | (2006.01) |

(52) U.S. Cl.
CPC .......... *A61B 5/0488* (2013.01); *A61B 5/1116* (2013.01); *A61B 5/165* (2013.01); *A61B 5/167* (2013.01); *A61B 5/442* (2013.01); *A61B 5/4848* (2013.01); *G06F 19/00* (2013.01); *G16H 50/20* (2018.01); *A61B 5/0205* (2013.01); *A61B 5/04* (2013.01); *A61B 5/0402* (2013.01); *A61B 5/11* (2013.01); *A61B 5/4803* (2013.01)

(58) Field of Classification Search
CPC ......... A61B 5/165; A61B 5/167; A61B 5/168; A61B 5/00; A61B 5/0048; G06F 19/3431; G06F 19/3437; G06F 19/3443
USPC ................. 600/300, 301, 481; 607/2; 705/2; 434/262; 340/539.12; 128/897, 898, 128/905; 1/300, 301, 481
See application file for complete search history.

(56) References Cited

U.S. PATENT DOCUMENTS

| | | | |
|---|---|---|---|
| 7,540,841 B2 | 6/2009 | Azzaro et al. | |
| 7,894,849 B2 | 2/2011 | Kass et al. | |
| 8,099,159 B2 | 1/2012 | Cook | |
| 8,677,281 B2* | 3/2014 | Morris | G06F 3/0481 715/772 |
| 2005/0245790 A1* | 11/2005 | Bergfalk | A61B 5/0002 600/300 |
| 2008/0214903 A1 | 9/2008 | Orbach | |
| 2009/0281414 A1 | 11/2009 | Feldman et al. | |
| 2009/0327068 A1* | 12/2009 | Pradeep | G16H 10/20 705/14.43 |
| 2011/0307029 A1* | 12/2011 | Hargrove | A61N 2/008 607/45 |
| 2012/0323087 A1* | 12/2012 | Leon Villeda | A61B 5/0402 600/301 |
| 2012/0330869 A1* | 12/2012 | Durham | G06N 5/022 706/16 |
| 2013/0009993 A1 | 1/2013 | Horseman | |
| 2013/0011819 A1 | 1/2013 | Horseman | |
| 2013/0012790 A1 | 1/2013 | Horseman | |
| 2013/0013331 A1 | 1/2013 | Horseman | |
| 2014/0057232 A1* | 2/2014 | Wetmore | G09B 19/00 434/236 |
| 2014/0171756 A1* | 6/2014 | Waldorf | A61B 3/032 600/301 |
| 2017/0231490 A1* | 8/2017 | Toth | A61B 3/113 600/558 |

OTHER PUBLICATIONS

Magrin-Chagnolleau, I., et al., "Application of time-frequency principal component analysis to text-independent speaker identification." Speed and Audio Processing, IEEE Transactions on, Sep. 2002, pp. 371,378, vol. 10, No. 6.

Xi-Lin L., et al., "Noncircular Principal Component Analysis and Its Application to Model Selection." Signal Processing, IEEE Transactions on, Oct. 2011, pp. 4516,4528; vol. 59, No. 10.

Schuller, B., et al., "Hidden Markov model-based speech emotion recognition." Acoustics, Speech, and Signal Processing, 2003. Proceedings. (ICASSP '03). 2003 IEEE International Conference on, Apr. 2003, vol. 2, no., pp. II, 1-4 vol. 2, 6-10.

Clauset, A., et al., "Hierarchical structure and the prediction of missing links in networks." Nature, May 2008, pp. 98-101, vol. 453.

Cohn, J.F., "Advances in Behavioral Science Using Automated Facial Image Analysis and Synthesis [Social Sciences]." Signal Processing Magazine, IEEE, Nov. 2010. pp. 128,133, vol. 27, No. 6.

Stephens, C., et al., "Autonormc specificity of basic emotions: Evidence from pattern classification and cluster analysis." Biological Psychology, Jul. 2010, pp. 463-473, vol. 84, No. 3.

Kurosh, M.H., et al., "Relationship of Perfectionism and Hardiness to Stress-Induced Physiological Responses." Procedia—Social and Behavioral Sciences, 2011, pp. 113-118, vol. 30.

Bach, D., et al., "Dynamic causal modeling of spontaneous fluctuations in skin conductance." Psychophysiology, Feb. 2011, pp. 252-257, vol. 48, No. 2.

Pei-Yang, H., et al., "The emotion recognition system with Heart Rate Variability and facial image features." Fuzzy Systems (FUZZ), 2011 IEEE International Conference on, Jun. 2011, pp. 1933,1940.

Ayadi, M., et al., "Survey on speech emotion recognition: Features, classification schemes, and databases," Pattern Recognition, Mar. 2011, pp. 572-587, vol. 44, No. 3.

Henderson, L., et al., "Real-time imaging of cortical areas involved in the generation of increases in skin sympathetic nerve activity when viewing emotionally charged images." NeuroImage, Aug. 2012, pp. 30-40, vol. 62, No. 1.

Stephens, C., et al., "Autonomic specificity of basic emotions: Evidence from pattern classification and cluster analysis." Biological Psychology, Jul. 2010, pp. 463-473, vol. 84, No. 3, Jul. 2010.

Yoshitomi, Y., et al., "Effect of sensor fusion for recognition of emotional states using voice, face image and thermal image of face." Robot and Human Interactive Communication, 2000. ROMAN 2000. Proceedings 9th IEEE International Workshop, 2000, pp. 178,183.

Kim, K.H., et al., "Emotion recognition system using short-term monitoring of physiological signals." Med Biol Eng Comput. May 2004, pp. 419-427, vol. 42 No. 3.

Mendes, W. B. "Assessing the autonomic nervous system." Methods in the Neurobiology of Social and Personality Psychology. Guilford Press, 2009. E. Harmon-Jones and J. Beer (Eds.).

Kolodyazhniy V., et al., "An affective computing approach to physiological emotion specificity: toward subject-independent and stimulus-independent classification of film-induced emotions." Psychophysiology. Jul. 2011, pp. 908-922, vol. 48 No. 7.

Maaoui, C.; Pruski, A.; Abdat, F., "Emotion recognition for humanmachine communication," Intelligent Robots and Systems, 2008. IROS 2008. IEEE/RSJ International Conference, Sep. 2008, pp. 1210, 1215.

Hajcak, G., et. al, "Event-Related Potentials, Emotion, and Emotion Regulation: An Integrative Review." Dev Neuropsychol. 2010, pp. 129-155, vol. 35 No. 2.

Kurzweil, R., "How to Create a Mind: The Secret of Human Thought Revealed." Ch. 7 (1st ed. 2012: pp. 135-157).

Gilbert, D., "Stumbling on Happiness." Ch. 3 (1st ed 2007; pp. 71-77).

International Search Report; PCT/US13/37604, dated Jul. 9, 2013.

* cited by examiner

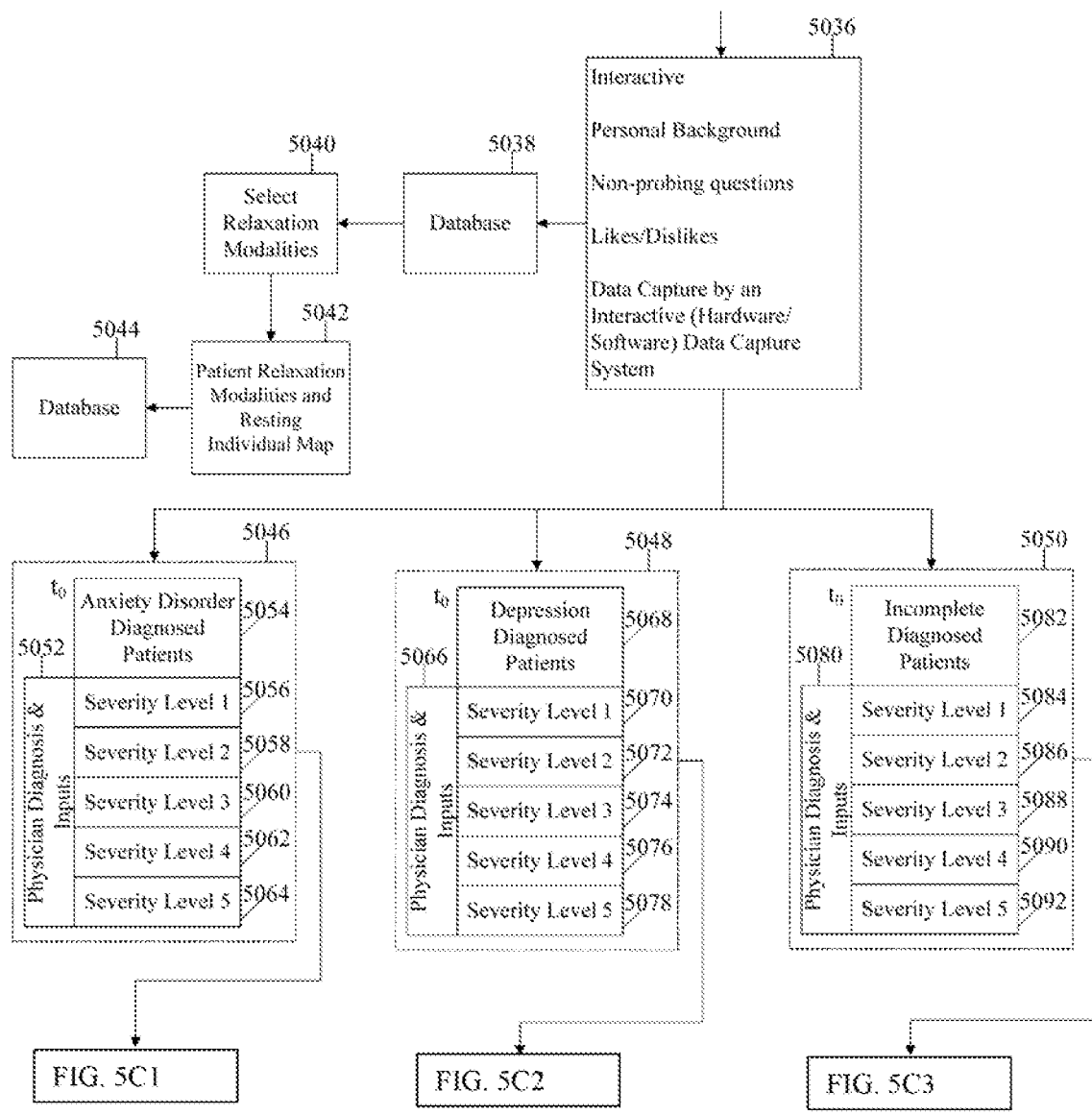

COGNITIVE BIOMETRIC SYSTEMS TO MONITOR EMOTIONS AND STRESS

PRIORITY STATEMENT

This application claims the benefit under 35 U.S.C. § 119(e) of Rau, U.S. Provisional Patent Application No. 61/637,259 that was filed on 22 Apr. 2012 which is incorporated herein by reference in its entirety.

FIELD OF THE INVENTION

This present invention relates to the field of mental health diagnosis and monitoring. More specifically, the invention relates to a method and apparatus for gathering autonomic physiological parametric data from a patient while the patient is subjected to changing emotion-inducing stimuli. The invention further processes the data by applying statistical, mathematical, and scientific analytical tools to infer changes in mental health.

BACKGROUND OF THE INVENTION

Stress can affect the physical and emotional well being of an individual. Emotional stress produces physical changes by stimulating the nervous system to respond. The body comes into a stressed state almost instantly when it detects any kind of threat, but the body must necessarily revert back to its normal state after a certain period of time. Reverting back to the normal state is not possible when the body is subjected to frequent or repetitive stress. Frequent or repetitive stress means that the amygdala and limbic systems are continuously overactive, so that the sympathetic nervous system keeps the body in a state of alert all the time, which does not allow the para-sympathetic nervous system to respond and bring the body to rest.

If the body is not reverted back to a normal restful state, the body systems that are suspended during the stress response cannot be resumed effectively. While the body is under this stressful state, the person can become anxious and depressed. In the depressive state, the brain is inundated with an unmanageable bombardment of negative thoughts. As the body continues to be in this heightened state, the linear progression from anxiety, to dysthymia, to depression and finally to post-traumatic stress disorder (PTSD) can be experienced, as depicted in FIG. 1.

This progression, however, need not be linear. FIG. 2 depicts one scenario where a sudden trauma or catastrophic event is experienced by an individual (example, e.g., death of a family member, natural disasters; or trauma from wars, accidents, and homicides.

Other changes can produce similar effects, but where the increased stress is experienced more gradually rather than instantaneous. These additional "gradual increase" stress-inducing events include various job stresses, chronic traffic, a bad relationship or marriage, performance or examination anxieties, rescue missions, combat fighting, or chronic health problems of loved ones.

Many published prior works exist that discuss various ways to handle patients in heightened stress states. This same body of prior work has evolved to include such therapeutic tools such as counseling techniques, group therapy, and prescription medications. Only recently, a few research papers have highlighted the importance and benefits of nontraditional modalities to help individuals exhibiting severe anxiety or mental stress.

Treatment and monitoring of mental health patients, more specifically those with mood disorders like anxiety and depression, has a limited set of objective biometric measurement tools available compared to the general health practices. Use of biometric measurement tools as monitoring devices is described in several patents. For example, U.S. Pat. No. 7,540,841 describes a system that collects data on an individual's daily activity to determine their mental health. U.S. Pat. No. 7,894,849 describes a method of collecting data through multiple sensors. WO2012108935 describes a health management system using a mobile communication device to communicate biometric sensor data through a server. US 20130009993, US 20130011819, US 20130012790, US 201300113331 all disclose a methodology to provide real-time feedback of health information of an employee from a set of health sensors while the employee is engaged in their work duties.

As described herein, the present invention provides new systems and methods for measuring objective, autonomic physiological parameters that allow for monitoring of emotional states in ways that were not previously contemplated.

SUMMARY OF THE INVENTION

In a first aspect, the present invention provides devices and methodologies for collecting a set of objective, biometric, patient measurements via an integrated system that records changes in an individual when subjected to varieties of stimuli through interactive modalities. The integrated system includes devices and tools to perform patient examinations; capture in real time patient-specific response data to various stimuli; perform data analysis to infer mental health changes; and map the changes in behavioral parameters.

In a second aspect, the present invention provides a system comprising a processor and associated software for applying data analytics on the basic response data elements and changes in a set of individual-specific behavioral aptitudes performance measures, and attitudes (IBAAA). Using this system, the present invention provides objective discriminant separation that can map the trend analysis in the full set and specific subsets of behavioral parameters.

In a third aspect, the present invention provides a device comprising hardware and software integration configured to record real time measurements of Autonomic Physiological Parameters (APPs). The APP data is captured and analyzed by a set of data analytical tools and algorithms to measure on a relative basis an individual's different emotions and coping skills at intervals over a period of time; and on a comparative basis longitudinally for many subjects by keeping track of gender, personal background, age, medical history and other likely relevant attributes. APPs include pulse rate; breathing (respiration) rate; blood pressure; changes in facial muscle tone; perspiration; facial galvanic conductance; facial skin tone; changes in pupil size; changes in eyelid fluttering and focuses; changes in sitting postures and bodily movements; movement of the leg and hand muscles; changes in voice pitch and tone; changes in facial muscles and expressions; and outputs of EEG, EMG, and EKG devices. The device can employ a combination of instruments to monitor and record one or more APPs.

In a fourth aspect, the present invention provides software interactive session modules that are stored within a computer. APP data is gathered during specifically-applied interactive sessions or modules (selected for each subject and session from a library of interactive sessions based on the case history of the individual being tested and/or information relating to the healthcare professional's recommended treatment plan and diagnosis) designed to generate natural emotions of a type and kind expected from a similar general population of cultural and national backgrounds. These modules are linked to a database, and can be selected from a library of validated session grouped for the application and patient type intended. The interactive sessions can be grouped into three different categories including: (1) Measurement Sessions and Metrics (MM); (2) Calming and Relaxing (CR); and (3) Mitigate and Desensitize (MD).

In a fifth aspect, the present invention provides a computer-implemented method applying techniques from hierarchical linear models (HLM), nonlinear mixed models, and generalized mixed models on the data output for data analytics. Traditional aggregation and cluster differentiation statistical techniques are used to present the data to healthcare decision makers with graphical and intuitive comparisons. These results are achieved by applying a mathematical algorithm incorporating sequential filtration of noise, expected deviations and anticipated correlated information of APPs, and changes while testing and applying statistical tools and techniques to generate the information outputs in graphical and comparative data formats.

In a sixth aspect, the present invention provides a reference database that performs a series of real-time analyses and computations, graphics-based applications, and data storage. The database can be connected to various remote-testing locations and stores all the data, statistical tools, and programs. An individual's records are stored in this database, such as those relating to the initiation of each query and an updated subject's history. These records can be kept in various required formats. Based upon the need of the query, these records can be sent to the decision makers in real-time.

In a seventh aspect, the present invention utilizes the results of other techniques such as MRI (and other scanning imaging methods), sleep studies and records, EEG (both in the sleep and awake situations) and blood tests, to benchmark the APP parameter changes according to this invention and correlate them with the findings from the other tests and techniques in order to develop the boundary conditions and different degrees of severity for each type of disorder.

BRIEF DESCRIPTION OF THE DRAWING

The present invention is described with reference to the accompanying drawings, which are not intended to limit the scope of the invention:

FIGS. 5A-5D are, when viewed together, comprise a single block diagram depicting one embodiment of the present invention's method for monitoring a patient's mental health during a treatment period;

DETAILED DESCRIPTION OF THE INVENTION

The following definitions are used herein:

The terms "patient," "subject," "employee," "soldier," "candidate," "individual," etc. . . . are used interchangeably to indicate someone who is tested using the methods and systems described herein.

The terms "healthcare professional," "nurse practitioner," "clinician," "physician, "psychiatrist," "psychologist," "decision maker," etc. . . . are used interchangeably to indicate someone who is involved with testing, analysis or treatment using the methods and/or systems described herein.

Figure 1:
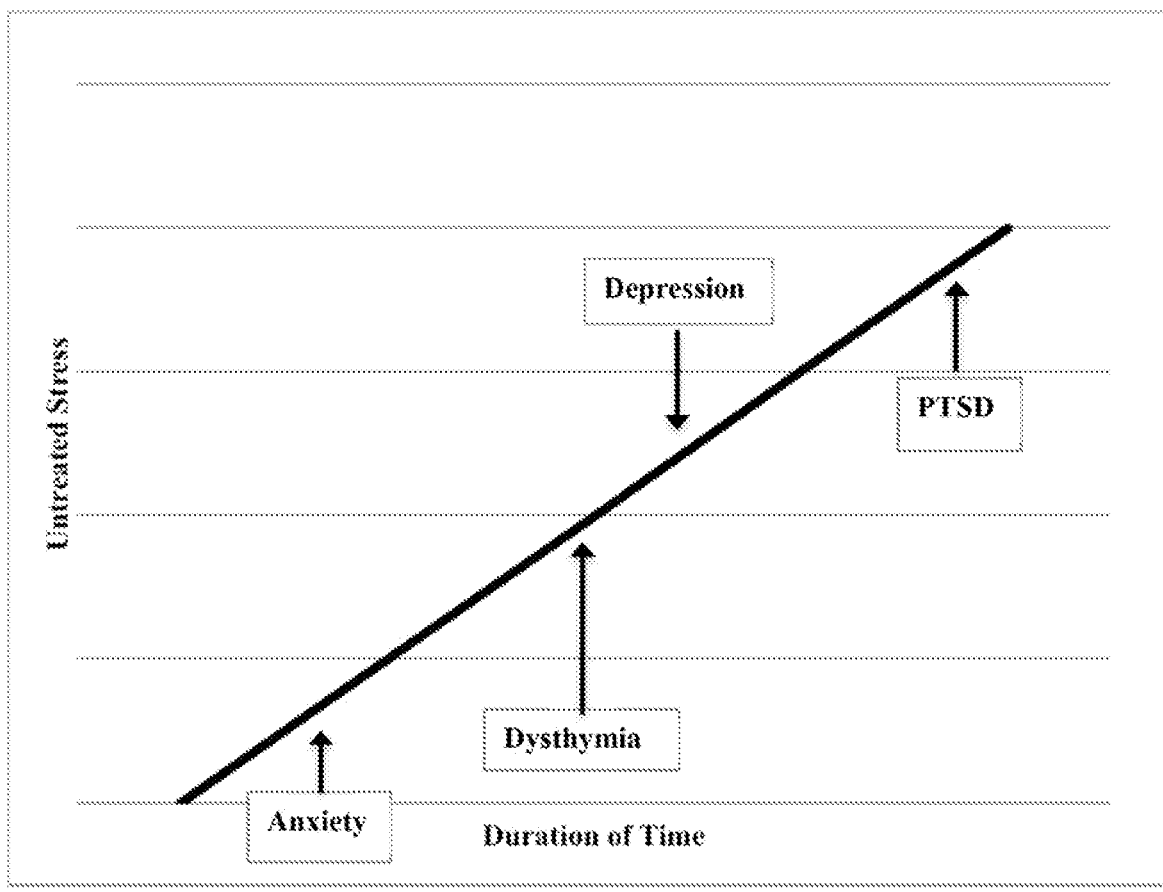
FIG. 1 is a graph depicting one scenario of the progression of stress vs. time.
Figure 2:
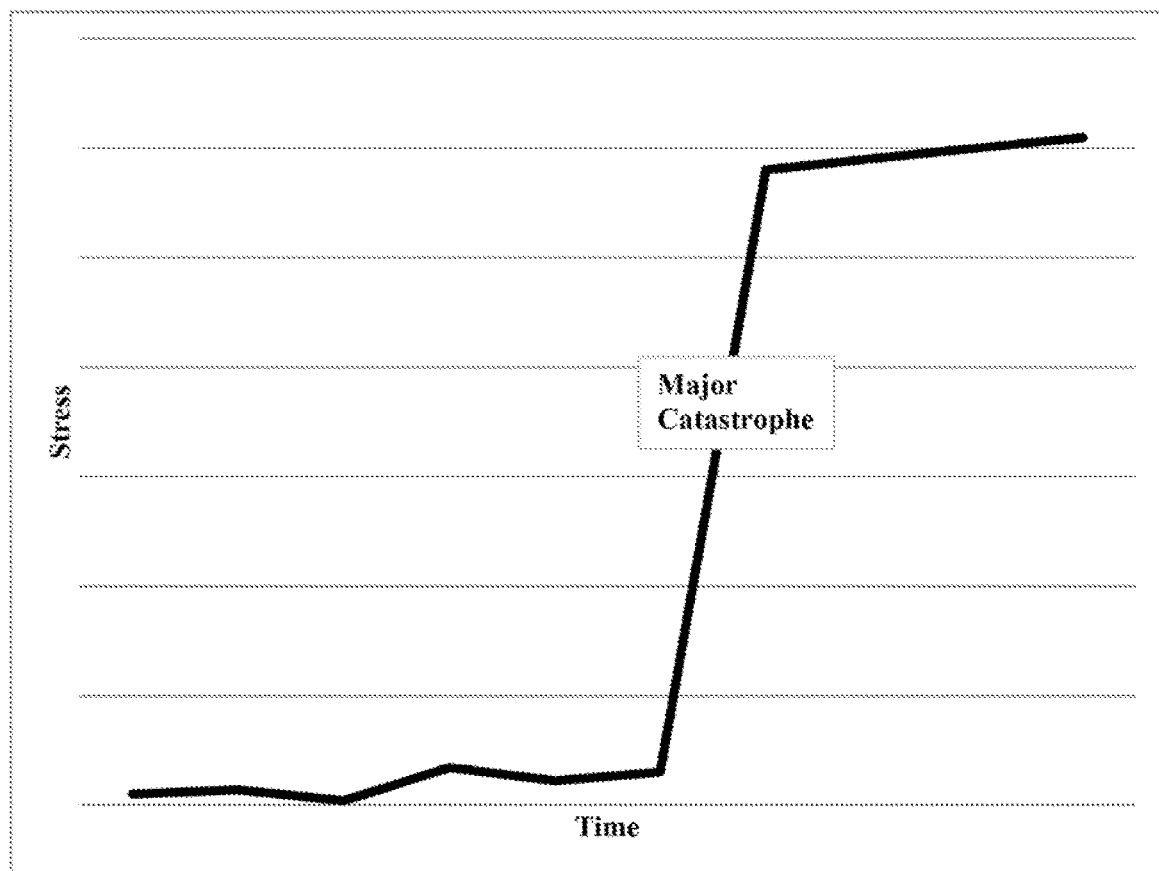
FIG. 2 is a graph depicting one scenario of the progression of stress with respect to time that might occur in response to a catastrophic situation.
Figure 3:
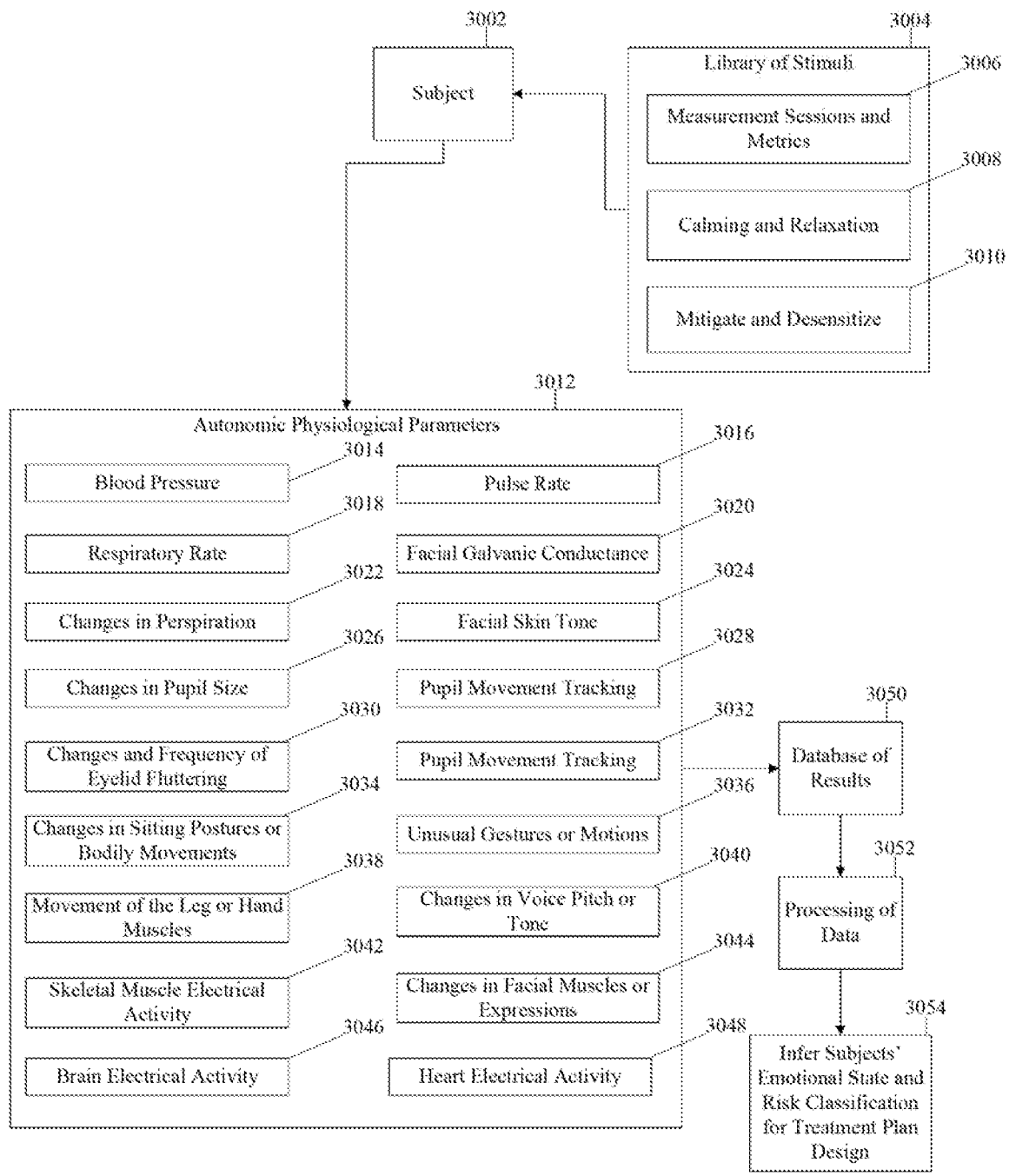
FIG. 3 is a block diagram depicting an overview of the invention.

In one embodiment, the present invention provides for the integration of testing, data collection, analysis, and inferences from the objective data beneficial for treatment-plan design to produce a better outcome for patients having mental disorders, as shown in FIG. 3. For example, the invention provides for measurement of APPs at various stages for specific degrees and types of mental disorders, wherein the measurements are tailored to specific groups of patients categorized by their common personal backgrounds and other characteristics such as gender, age, race, education, economical status and geographical upbringing. Among the parameters measured are the patient's reactions to various types of induced stimuli, such as those eliciting calming, relaxation, pleasure, sadness, or anxiety as well as stress-type of responses specific to particular mental disorders. The library of stimuli 3004 are categorized into: measurement sessions and metrics 3006, calming and relaxation 3008, and mitigate and desensitize 3010.

There can be two types of APP data capturing situations. In one situation, the individual undergoes testing with various stimuli in addition to intensive personal questioning by a clinical psychologist or psychiatrist (clinician). In a second type of session, the clinician may or may not be present and the individual is subjected to the testing by the stimuli alone in an examination room. The individual interacts with the stimuli through various methodologies including: intensive personal questioning by a healthcare professional; having an individual play video games that send stimuli through visual, oral, aural and kinesthetic modes; answering validated psychometric/psychiatric tests that capture oral and written responses; rapid fire questioning using provocative questions in clinician-present sessions related to the characteristics and backgrounds of the patients; mood relaxation and calming sessions; video and audio combinations designed to assess specific aptitudes and performances; visual and audio stimuli of certain war footages; and specific experiences that might have caused a specific mood disorder.

These stimuli and questioning sessions may last, for example, 20-40 minutes and are preferably administered by suitably trained healthcare professionals. Preferably, the subject is isolated in an examination room specially designed and equipped to capture varieties of APPs 3012 (monitored by a healthcare professional from a different room to intervene in case of any emergency). The data capturing equipment is preferably designed for capturing involuntary muscle movements; blood flow changes to the face 3024; skin conductivity 3020; sweat formation; changes in facial muscles and expressions 3044; blood pressure 3014; perspiration 3022; pulse changes 3016; speech and tone changes 3040; changes in pupil sizes 3026; changes and frequency of eyelid fluttering 3030; pupil movement tracking 3032; limb muscle twitches/changes 3038; postural changes in the sitting position 3034; electroencephalograms (EEG) 3046; electromyograms (EMG) 3042; and electrocardiograms (EKG) 3048.

These APPs are continuously sensed and recorded, and the resulting data are captured during interactive sessions using selected stimuli. The real-time capture of APP data is correlated against observed state changes of the individuals. These computer-administered stimuli include any combination of video games, validated psychiatric and psychological tests, films, or music. A library of these stimuli sessions can be developed and categorized to induce specific emotional reactions in patients. For example, these sessions can be designed to induce painful modes similar to an individual's prior personal experiences, mood relaxation, pleasant modes, or agitating modes of anger and sorrow.

The APP data collection is accomplished through different sensors and monitors that are integrated through software that operates on, communicates, and interfaces with various hardware/software combinations. The hardware/monitoring devices can include: a chair specially designed with sensors to capture the muscle/limb change; a glove for capturing blood pressure, heart rate, pulse, muscle twitching, and/or skin conductivity; a belt for capturing respiratory changes; and a hat designed for measuring blood flow changes from the ear lobe and electrical impulses from the brain and any other skin conductivity and pulse changes.

A number of video cameras with a combination of optical and infrared sensors designed to capture pupil changes and movements or eyelid fluttering (optical sensors), sweat changes (combination of optical and IR) and postural movements (optical) are to be strategically located both on a monitor screen and different positions in an examination room. Additionally, microphones are suitably located and employed for speech capturing and analyzing devices.

The digital and analog inputs for APP data capturing devices are administered through a hardware/software-integrated device. The data capturing electronic board and/or integrated chip with input and output leads will generate a digital output from recorded digital waveforms. These digitized records will be stored. For each of the inputs, the hardware will also record continuously while superimposing or marking the specific behavioral stimuli induced through the interactive sessions/professional questioning. Additionally, the hardware computes the changes in each and grouped APPs from the set of executable programs loaded into this hardware module. The programming identifies the specific stimuli points on the timeline with the induced changes in each and subgroup of APP for each person and session. Although some of these changes might be very subtle, the hardware is designed to have the flexibility to calibrate for a number of mood disorders and individuals.

These monitors can be mated with programming and other devices for signal display and continuous data recording through microprocessor board/digital signal processing chips. These outputs are fed into the computers/laptops to display, communicate, and maintain digital records in the database for each patient. At the end of each session, the data collected is maintained as session data (time, date, etc. . . . ) and then added to the individual's records in the database 3050. At the beginning of the session individuals' prerecorded session data will be pulled from the database and will be ready for update at the end of the session. The session will have running software to compare changes between the current and previous sessions of the individual.

The theory behind the present invention is that human beings exhibit different emotional and involuntary responses while relaxing and being exposed to various stimuli. Rather than the absolute values of the APPs, their changes (individually and in combination) for each patient (healthy and normal, or suffering from a mood disorder) can be individual-specific and related to a specific mood disorder the patient may have. Repetitive measurements and collection of a large number of parameters and analysis of the same allows the minimization of variations (individual to individual) and reduces the standard deviation.

The APP data and computed changes are collected in a controlled environment through specially preset procedures and processes, and yield valuable information after application of relevant mathematical, statistical, and scientific data analytics and techniques 3052. The outputs of the processing of the APP data changes via the analysis tools set are provided to the healthcare professionals for their use. In collaboration with the clinician, the outputs will be mapped into the mental states as defined by the healthcare professionals 3054. The APP base value changes that are measured in each person are combined by utilizing the following: personal backgrounds; work histories (e.g., high stress environment or job assignments), specific mood disorders diagnosed (e.g., PTSD, OCD, and generalized anxiety disorder); and personal life situations faced by the individual that may result in grief, anxiety, or depression disorders.

This data analysis is performed by the application of computer programs and analytical techniques belonging to a category of mathematics known in the art as "Big Data Analytics." The present invention applies suitably modified variations of mathematical, statistical, and scientific techniques such as inter- and intra-subject multivariate analysis, Bayesian Inferences, and other mathematical techniques in the form of a number of algorithms developed for application and employed at different junctures of the data analysis. The database with the large volumes of captured APP data for each individual in the group studied is disclosed below, including the design of a database structure for the data organization. This data organization and database management provides real-time feedback and record management for the patient being tested.

Figure 4:
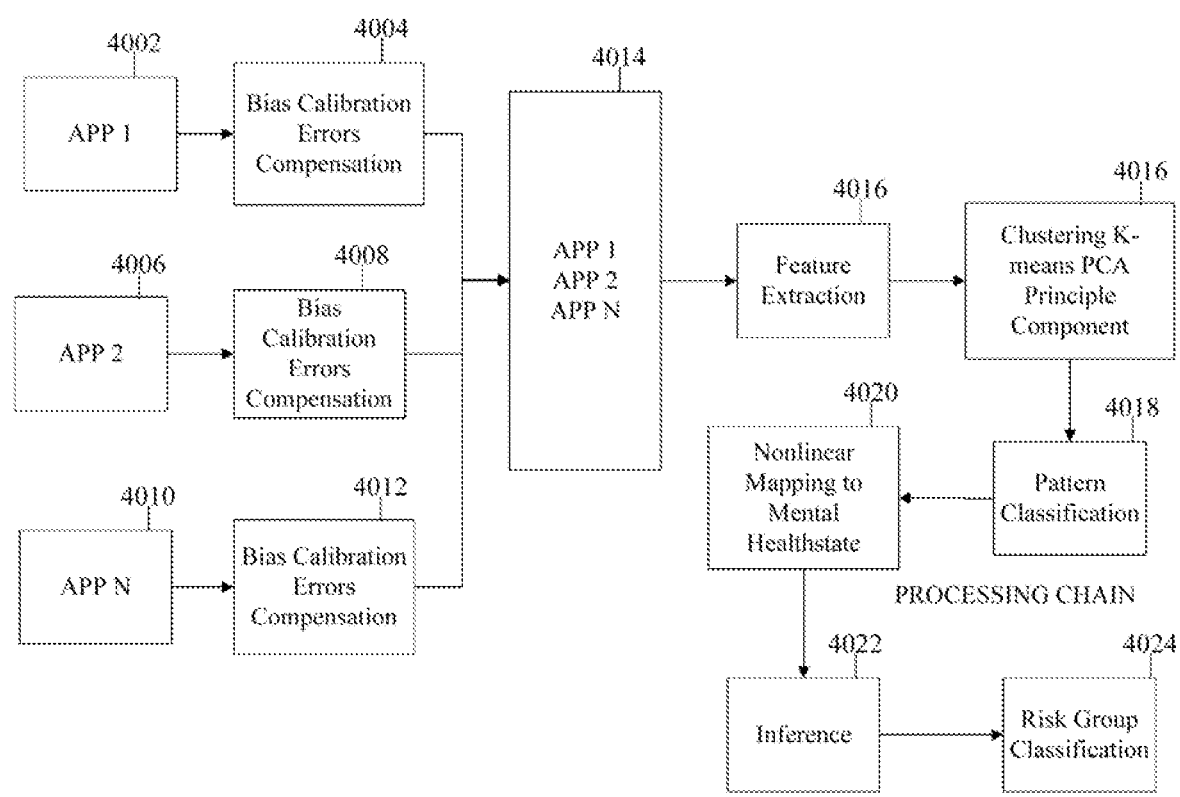
FIG. 4 is a block diagram depicting the data processing for the APPs.

As shown in FIG. 4, the database of APP vectors 4014 is processed using a variety of algorithms which provide: (1) calibration corrections and biasing error estimations of each instrument used in data acquisition 4004, 4008, 4012; (2) feature extractions 4016 such as means, variances, kurtosis, frequencies characteristic of time series data, or segments of time series records from EEG data; (3) processing the selected feature set into clusters using clustering algorithms such as K-Means clustering 4018, principle component analysis; and (4) classifying the extracted clusters 4018 into patterns using pattern classification algorithms. The end result of this processing chain is to map the patterns onto a set of emotional states 4020 as defined by clinicians and medical practitioners, such as emotional mood disorders. This will enable medical practitioner to detect possible change points in the underlying processes and infer specific adverse or positive change 4022 over in the underlying processes due to significant changes in individual's physiological conditions or from the treatment plans or regimens used 4024. Continued monitoring of the emotional states as quantified herein enables a medical practitioner to train subjects in improving their coping skills and resiliency towards a disorder in response to incremental changes in the patient's condition.

Another embodiment of the invention relates to nonclinical application with multiple versions of APP data capturing devices. These versions differ in terms of APP device combinations, their sensitivity and test administering field locations to incorporate rugged features. Trained technicians rather than mental health professionals administer these test sessions.

All these APP data devices are integrated to a computer with wireless data transmission capability. Cameras output is recorded. Other APP data capture is as continuous signals for certain APPs and as periodically sampled data (either digital values or signal wave forms). This invention has two distinct components for each of the two above applications. The first component is mapping the different emotions and changes in these specific emotions between different testing periods. Each emotion is identified based on the stimuli used. A specific stimulus is labeled as that emotion designed or expected to be elicited from the subject. The stimulus for each emotion is further categorized by three or more levels of intensity. The initial period of each testing session is the emotion mapping and mostly have passive in nature of physical response inputs by the individual. Typically, the APP expected to yield significant valuable results are pupil width changes, facial expression changes, IR part of the video and EEG implemented in select cases.

In clinical applications, the second component will map the coping skills. In nonclinical applications, the second component will map the changes in resilience of an individual and measure the benefits, if any, of the individual resilience improvement trainings and programs by identifying the positive improvements before/after, and after a set interval subsequent to those programs. The effectiveness of these programs is evaluated by comparing the results from larger sample sizes of individuals as a group in addition to comparing individual level information.

The data collected from the healthy (nonclinical) and sick (clinical) populations comprising large samples of individuals with repeated frequent testing sessions over a 2 to 4 year period is a part of the large database. An average of four-per-year testing sessions with a minimum of two sessions per year is the designed frequencies for this data. Each individual testing session data capture satisfies the accepted definition of 'Big Data' as having volume, velocity and variety. The raw data from each session is processed at the initial testing station to compute the changes. The raw data and the processed information are transferred to the database. This information for different groups of individuals processed by applying different analytical techniques is utilized to generate a number of outputs. Some of these summary results derived through these computations are:
1. Deviation maps highlighting statistically significant deviations (from measures of compactness around the central value in a multidimensional space) for types of emotions grouped as positive, neutral and negative for a level of stimulus intensity of that type of emotion defined. These will serve as baselines for an individual, individuals grouped by their background characteristics and overall population tested. A summary index, developed from this information, is used to visually highlight an individual's relative positioning for each emotion and a combination of emotions. This index is also used to compare the changes for each individual between different test sessions over a period of time. These changes for different groups of individuals and the larger population groups are also continuously computed and updated as the database is progressively increased as the number of test sessions and individuals increase. These comparisons are referred to as longitudinal intra and inter personal comparisons.
2. The coping skills for the clinical testing sessions and the resilience maintenance for the nonclinical testing sessions are mapped using interactive stimuli designed for active inputs by the individuals tested. Analytical results of the inter- and inter-personal longitudinal changes between sessions, type of stimuli and groups based on similar personal characteristics are combined to form a number of indexes to provide summary changes for easier visualization and tracking. The different indexes for nonclinical and clinical databases are used to compare and develop significant direction and dimension deviations of different sets of APPs for specific disorders and potential clustering of specific APPs within the clusters to provide specific diagnostic markers for different types of anxiety or depression or other types of mental health disorders.
3. In resiliency tracking application for healthy individuals and measuring changes in the coping skills for patients with different mental disorders (improving the coping skills is a major objective of mental health treatments through therapy or medications or combination of therapy and medicines) application, linking the sleep records recommended by the clinicians as prescribed, personal records of general routine mental and physical health records, any other relevant information gathered from personal and professional life changes and general health screenings including genetic tests are integrated to infer changes in emotional status.
4. A set of indices to track the stability and resilience of the emotional status of individuals in general or those employed in high stress work situations by combining relevant changes of APPs found significant for each type of individual groups are used.
5. A set of indices to track changes in mental health patients' coping skills and efficacy of prescribed treatments over time by combining relevant changes of APPs found significant for each type of mental health disorder or disease.
6. The facial expression data set from the large nonclinical and clinical components of the databases is used to develop atypical facial expressions and specific muscular combinations associated for adverse and high stress emotions. This information is used as reference information for the catastrophic disaster assistance systems. The reference information is stored in a computer system maintained at the designated disaster evacuation and recovery centers. Video cameras as a part of emergency management are programmed to take certain number of frames and relevant facial features of the evacuated individuals. Based on this risk analysis, this data is compared to the reference data already stored through a software program to identify the individuals affected adversely. Integrating the disaster experience history from the subject and the other persons who may have observed the subject, the severity levels of stress emotions developed can be further classified for these individuals. Scarce physical and professional resources can be targeted to these needy individuals during the critical phases of disruption and early recovery periods during and after the catastrophes or disasters.

Database of the Invention

Figure 10:
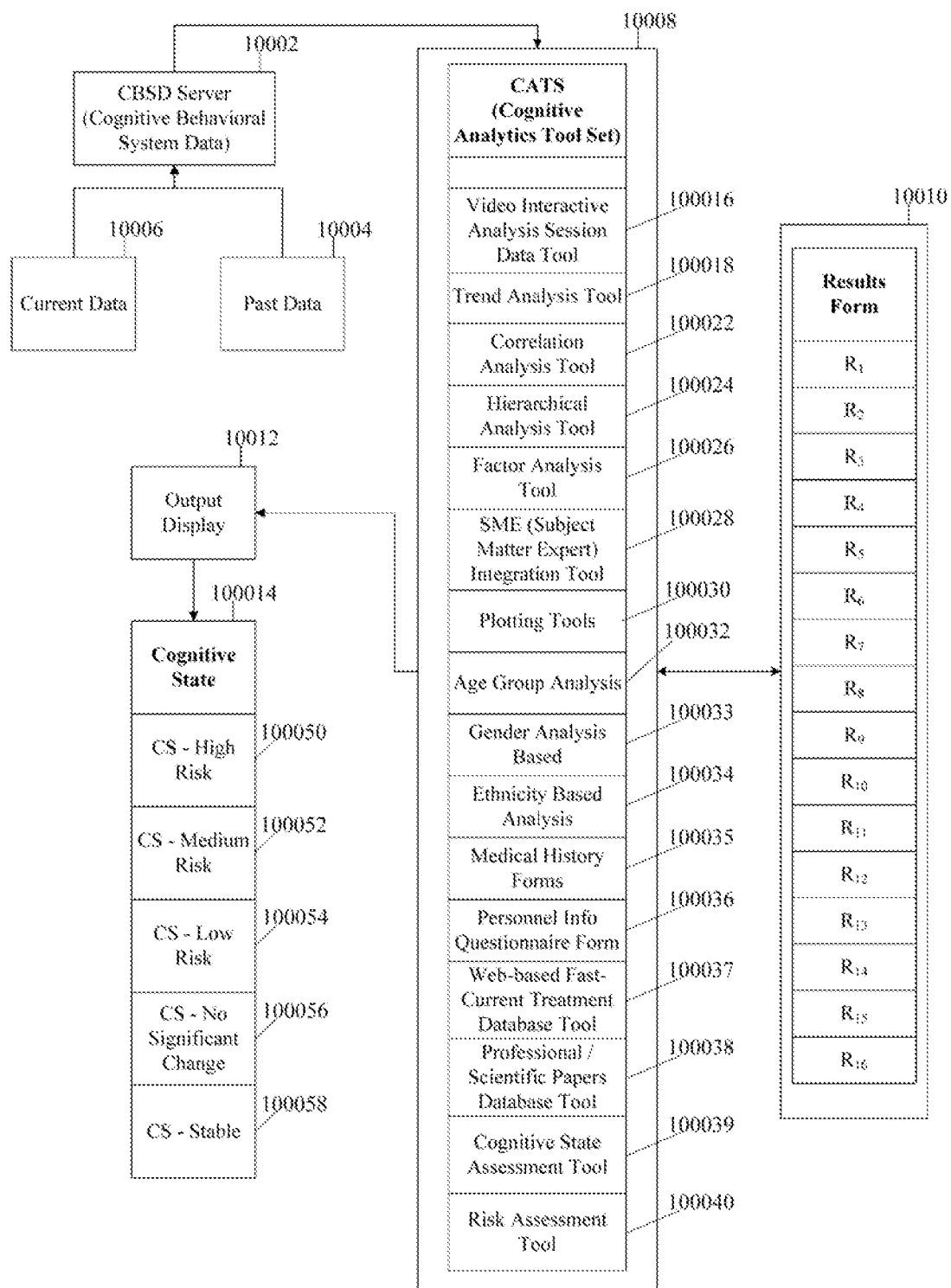
FIG. 10 is a block diagram depicting an example of the database of the invention.

As in devices intended to be used with a very large number of patients to collect and analyze very large amount of data, the processing and data component of the present invention can be designed to include a server coupled to a plurality of modular servers, such as modular server 10000 (whose functionality is schematically displayed in FIG. 10). The server contains many modular servers (e.g. 10000) interconnected through software. As represented in FIG. 10, for every new testing or treatment session, data 10006 from the session is stored and integrated on modular server 10000 with the data of prior sessions 10004 to generate a Cognitive Behavioral System Data set (CBSD) 10002. A number of algorithms developed from analytical techniques specifically developed for each cognitive analytical tool, as presented at block 10008, interact with the CBSD after each session's completion.

Various cognitive, analytical tool set elements 10016, 10018, 10022, 10024, 10026, 10028, 10030, 10032, 10033, 10034, 10035, 10036, 10037, 10038, 10039, and 10040, are shown at block 10008 of FIG. 10. The plurality of tools in 10016-10040 is provided for analyzing various data obtained, and maintained within the cognitive behavioral data set 10002. The data from the CBSD server is analyzed with these tools to achieve certain results, as shown in the results form at block 10010 of FIG. 10. These results are stored in results forms and tables 10010, output displays to the decision makers 10012, with the cognitive states of the subject categorized 10014 as per the severity and risk, by applying the validated filters from the validated summarized information in the fully integrated and operational status.

Normalizing database schema coupled with denormalization techniques to improve performance is warranted in this design. The customization for this application is achieved through the described design features employed into the well-accepted database providers (Oracle and IBM) with the necessary hardware selection. For the statistical analysis and report presentation one of the major software packages (SPSS, SAS etc.) are used in conjunction with the analytical tool set developed specifically for this. A person with experience and skills in this field can integrate these features as described to design/develop this application. The user needs are supported with the front end GUI (Graphical User Interface) with WIMP (windows, icons, menus, and pointer) through the standard Structured Query language (SQL) or other variants.

Standard operational features that are part of this system can include: the data collected (acquired in interviews, video interactive sessions and information coming from any APP monitoring devices on the patient) transferred online; critical information triggering an alert to medical practitioners; the stored results of offline analysis; any critical indicators seen in the analysis automatically sent as alerts to the decision makers; the data, as well as the analysis results, saved as files to a web server with real time access by healthcare professionals; a simple search capability with a user friendly GUI provided to the health professionals/users as decision aids for treatment; the stored database saving relevant data received from various sites; and archived databases stored on secure servers automatically updated while always archiving a backup copy to protect the information. This database utilizes Hadoop software framework to process this information.

Hadoop, an open-sourced Apache software package, is currently one of the most popular methods of distributed data processing. Hadoop processes large quantities of data by distributing the data among nodes within a cluster and utilizing algorithms to process the data. The data cataloged for each patient data, and the correlated results, are processed with Hadoop framework to search the appropriate sessions from the interactive session library to be used on future patients.

Specific Applications of the Invention

Further features and advantages of the invention, as well as the structure and operation of various embodiments of the invention, are described in the applications below with reference to the accompanying drawings. The drawing in which an element first appears is typically indicated by the corresponding reference number. It is understood that various aspects and embodiments of the invention described in these applications may be used outside the context of the specific application.

i) Integrated Treatment Plan for Patients with Mental Disorders

FIG. 5 is a block diagram, depicting one application of this invention's system of measuring the changes in a patient's mental health during their treatment period. This system has applications, for example, in Veterans Health Administration (VA) or Military Hospitals.

In this system, the patient has already been diagnosed 5002 with a mental disorder. The healthcare professional will decide the treatment plan depending on the type of mental disorder. If the patient is diagnosed with a general mood disorder 5004, the prognosis will be limited to only medical problems 5006 and the recommendation to the healthcare professional will be to use the regular diagnosis methodologies 5008.

However, if the patient is diagnosed with either one or a combination of medical and mood disorders 5010, the healthcare professional will have to do additional testing to diagnose the patient for only mood disorders 5012 or the patient having both mood disorders 5016 and medical problems 5018. Depending on the prognosis of the patient, a treatment plan 5014/5020 will be used on the patient.

Figure 5A:
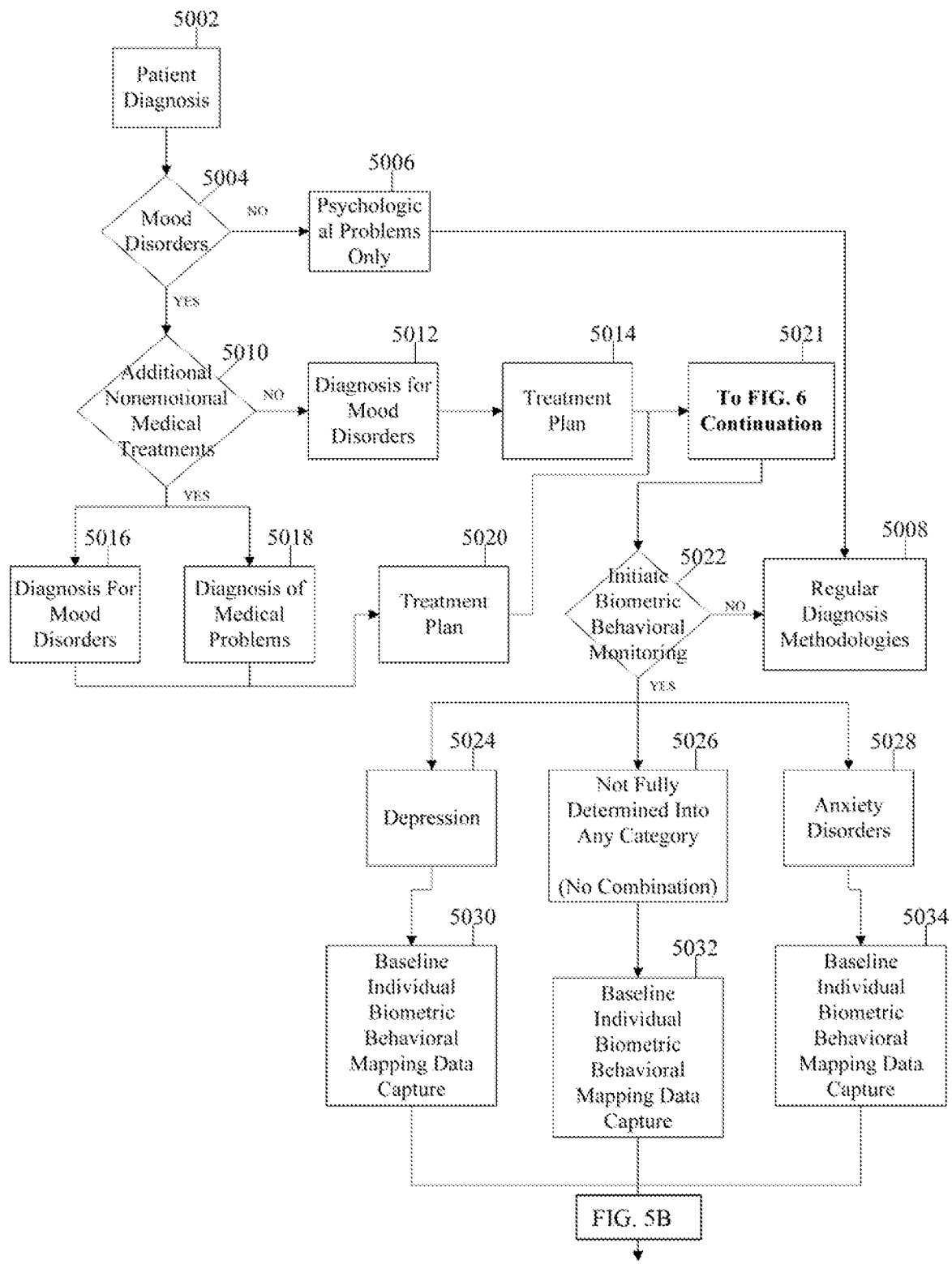
Figure 5C:
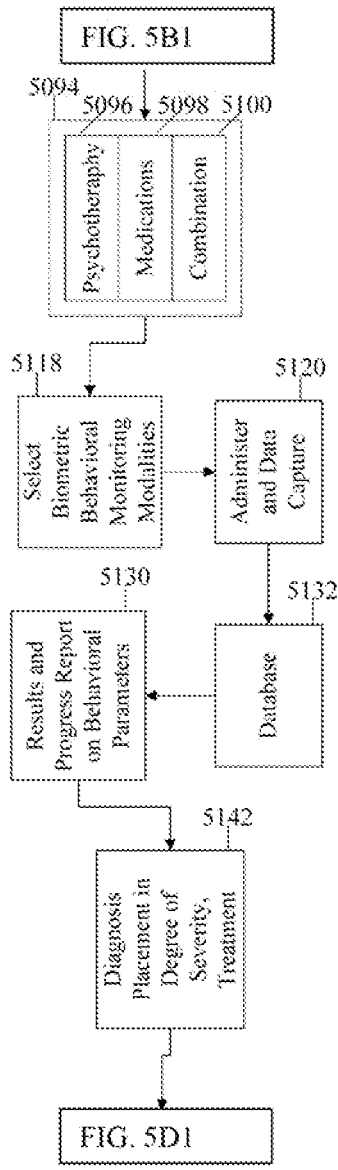
Figure 5C:
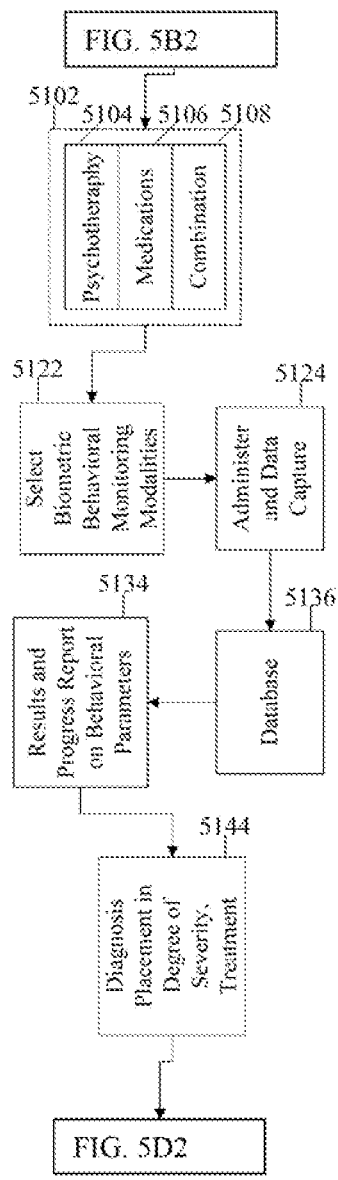
Figure 5C:
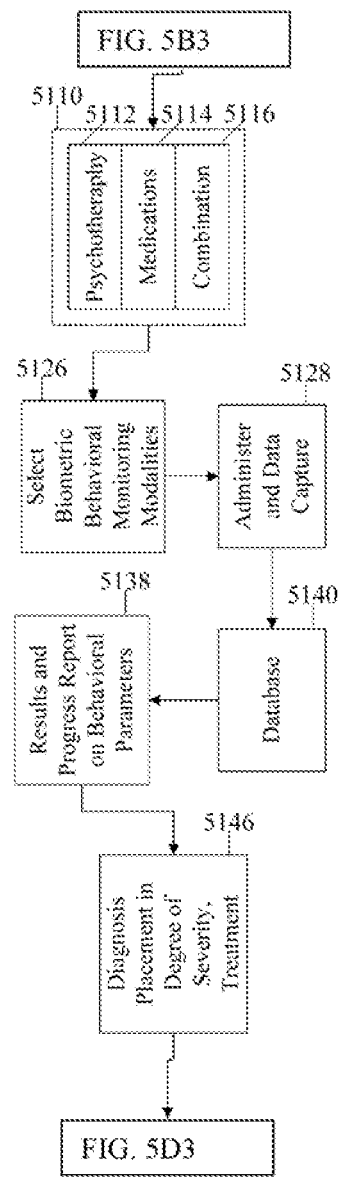
Figure 5D:
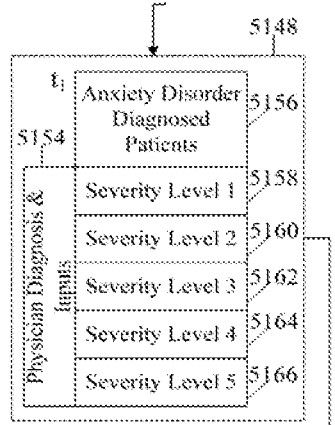
Figure 5D:
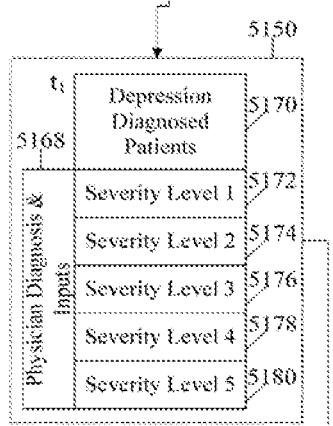
Figure 5D:
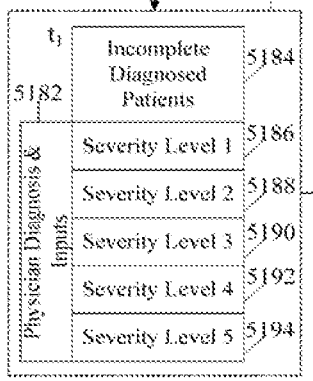
Figure 5D:
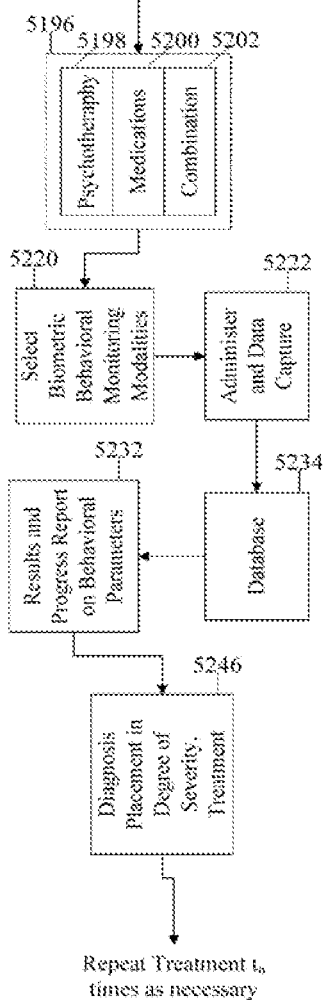
Figure 5D:
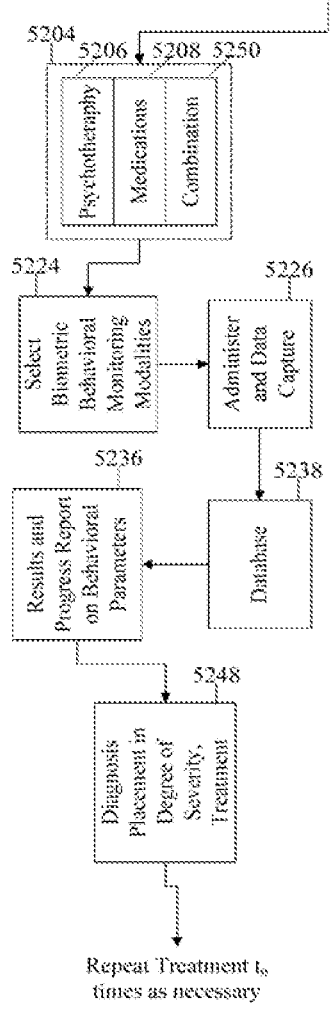
Figure 5D:
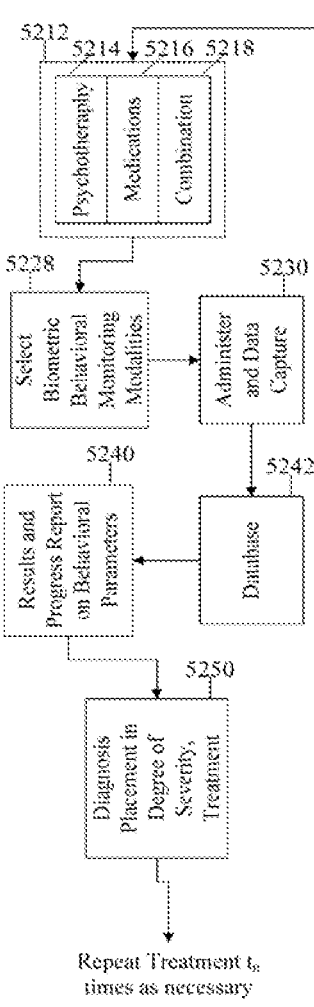
Figure 6A:
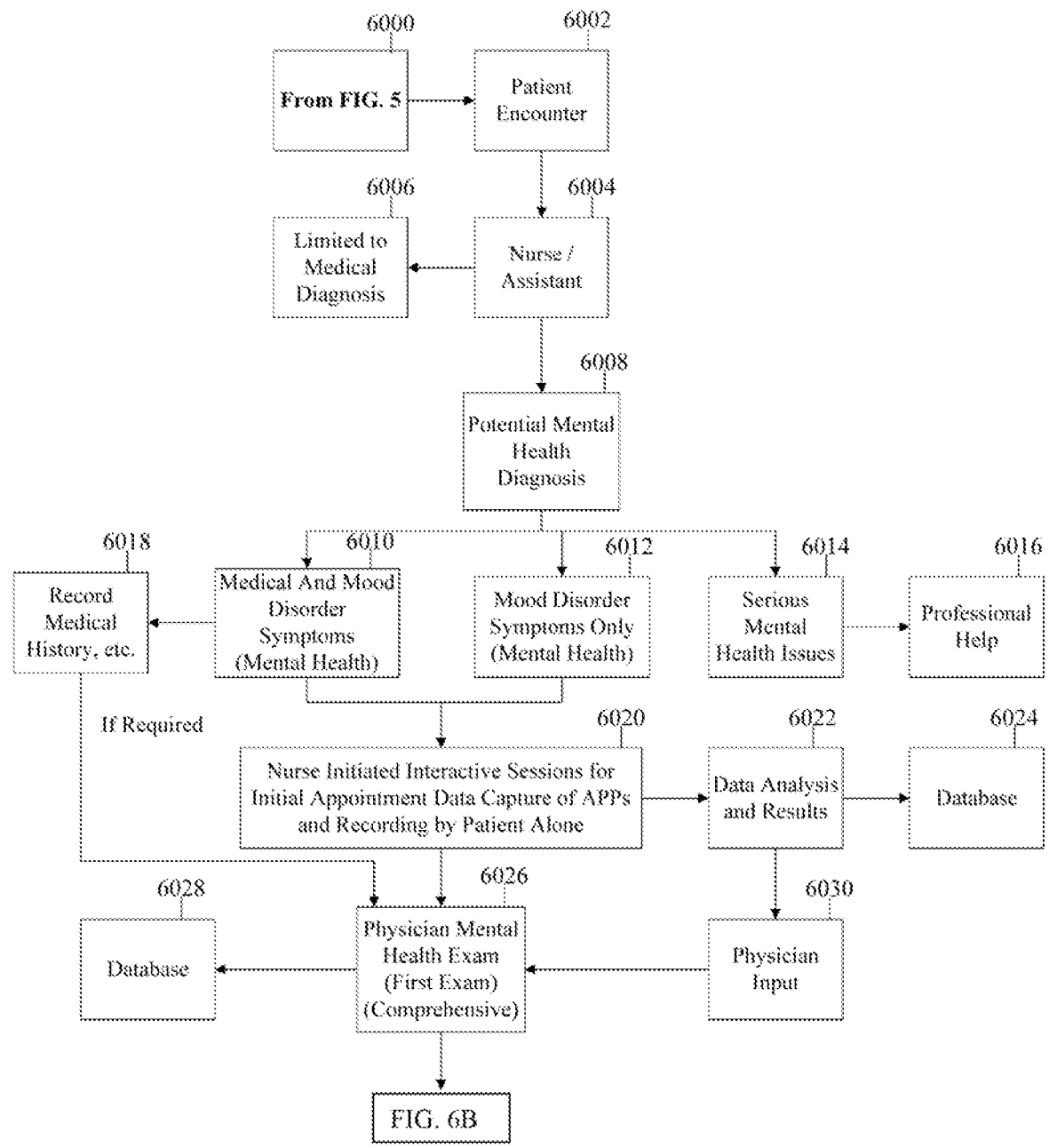
FIGS. 6A and 6B, when viewed together, comprise a block diagram depicting a system for providing a treatment regime to treat patients with mental disorders.

Referring to FIG. 6, a system that creates a treatment plan for mental disorders is illustrated. After being diagnosed with both medical and mood problems, the patient has an initial encounter 6002 with a healthcare professional 6004. Either the original diagnosis (see 5012, FIG. 5) is used, or another diagnosis 6008 may be made to categorize the patient into more specific categories for determining the appropriate treatment plan for the patient. If the healthcare professional believes that the patient does not have a mental illness, a new diagnosis 6004 of the patient will be rendered wherein the diagnosed disorders have limited associated medical issues.

If a patient is diagnosed as having a mental disorder, the patient is then grouped into one category (of a plurality of possible categories) that is appropriate for his mental illness. In FIG. 6, the three shown categories include Medical and Mood Disorder Symptoms 6010, Mood Disorder Symptoms Only 6012, or Serious Mental Health Issues 6014. For patients categorized into serious mental health issues, the system can recommend to the healthcare professional that the patient seek appropriate professional help 6016. In the cases wherein a patient is experiencing both mood disorder and medical disorder symptoms, the healthcare professional initiates an appointment for an interactive session to capture APP data and recordings of the patient 6020. Any further medical history of the patient 6018 can be recorded that might be beneficial in the patient's treatment. After the APPs and recordings of the patient are captured, the data is analyzed, and the data analytics and any results from the testing 6022 are fed back to the database 6024 and can be accessed by the healthcare professional overseeing the patient's case 6030. The results and findings from the clinician's initial mental health examination sent to the database 6028.

Based upon the first mental health exam 6026, and any further APP data or other inputs 6036 from the database 6036, a diagnosed treatment plan 1 6032 (FIG. 6B) commences or the patient. Once the first exam has been completed, the patient is grouped into an appropriate diagnoses category so that an appropriate treatment plan can be initiated for the patient. The patient is categorized according to results of the patient's exam, which can include one of the five categories based upon the exam results: A) Acute Stress 6038, B) PTSD 6040, C) Other Anxiety Disorders 6042, D) Suicide Ideation 6044, and E) Personality Disorders 6046. Subject to the patient's grouping, a variety of different treatment options will be available. If the patient is grouped into the acute stress category A) 6038, the physician can use treatments appropriate for treating acute stress, such as: psychotherapy, medications, stress reduction, and any additional modalities shown in block 6048A. Patients who are experiencing PTSD are grouped into category B) 6040 and are treated with the techniques set forth in block 6048B. If the patient has been categorized as suffering from other anxiety disorders C) 6042 such as generalized anxiety disorders, other phobias, obsessive-compulsive disorder, panic disorders, and social anxiety disorders, the patient is then treated with techniques set forth in block 6048C, psychotherapy, medication, and stress reduction, individualized modalities and other appropriate treatment regimes.

If the patient is showing signs of suicide ideation, or has been grouped into category D) 6044, the healthcare professional can use medications, therapy, and individualized stress reduction modalities 6050 to help prevent the patient from attempting suicide. Another option available to the healthcare professional is to utilize a portable APP monitoring device and an event mode activation device 6052 that can be worn by the patient. This portable APP monitoring device 6052 is designed to monitor the patient's vitals and any implications of negative thoughts. This device can be then used to notify the patient and/or the healthcare professional when any signs of suicidal ideation arise. Structured responses can be administered by the patient himself and followed by interventions from (1) distantly-located healthcare professionals via phone or (2) Emergency Medical Technicians (EMTs) speedily reaching the patient (in case of patient non-responsiveness or emergencies), as is typical in the current practice of the suicide ideation treatment/prevention approaches used in Veterans Administration hospitals and other hospital systems.

If the patient is experiencing personality disorders or is grouped into category E) 6046, the medical practitioner can use psychotherapy, medications, and individualized stress reduction modalities 6054 to treat the patient. When the medical practitioner is performing the treatment process, the system will provide the practitioner with an option to utilize APP recording 6056 for any further inputs in the treatment process; or instead to use traditional modalities. It is important to note that during the treatment process, the patient can experience symptoms identified by the other categories during the treatment process. Depending on how the new symptoms have arisen, the healthcare professional can change the treatment methodologies used on the patient to a different group.

Once the first treatment plan is completed, a second treatment plan assessment 6058 will be used on the patient, with the updated results sent to the database 6060. This second treatment plan assessment includes re-categorizing the patients into one of several appropriate categories. In the instant example, four categories of next tier assessment categories are employed for the patient: A) Category A 6062; B) Category B 6064; C) Category C 6066; or Category D) 6068. The primary differentiation point between the tour categories 6062, 6064, 6066 and 6068 is the amount of progress (or lack of progress) made by the patient during the first treatment plan.

As the patient progresses in their treatment, treatment plan 3 6070 can be devised for the patient. Treatment Plan 3 6070 should be repeated on the patient as often as it is necessary to achieve the desired progress in the patient's mental health condition. At some point, after an appropriate number of repetitions of treatment plan 3 6070, the patients can be re-evaluated, and re-categorized into four categories that differentiate the patients based on the progress that they have made using the treatment modalities of the present invention. These categories include Category A 6072; Category B 6074; Category C 6076 and Category D 6078. Treatment plan 3 is repeated as necessary until treatment plan N 6080 is used with the same modalities and grouping into specific categories A) 6072, B) 6074, C) 6076, and D) 6078, and so on.

This depiction presents one scenario of how a treatment plan can be implemented in a health facility or remotely. If there are a variety of severity levels of the mental disorder, FIG. 5 further illustrates treatment plans for those mental health cases.

Once the diagnosis of the mood or medical disorders has been completed, the healthcare professional can initiate biometric behavioral monitoring (BBM) 5022 (FIG. 5A) on the subject. During this BBM 5022, the subject is placed into an appropriate category that relates to the type of mental health disorder the subject has been diagnosed with. In the illustration shown in FIG. 5, three categories of mental disorders are shown: Depression 5024, Anxiety Disorders 5028, and Not Fully Developed into Any Category or No Combination of the disorders 5026.

A baseline of biometric mapping data is then captured at 5030, 5032, and 5034. The captured information includes such things as personal background information, information learned from non-probing questions; information about the patient's strong feelings, likes and dislikes, and other data captured through the interaction between the patient and the testing device, as shown at block 5036 (FIG. 5B).

All of this information is sent to the database 5038, and processed. The outputs from this processing will be used to create the various relaxation modalities 5040 that are appropriate for the particular patient. The various treatment modalities 5040 chosen for the patient are dependent upon the type of disorder exhibited, such as an anxiety disorder 5046, 5054; a depression disorder 5048, 5068; or an incomplete diagnosed disorder 5050, 5082.

Figure 6B:
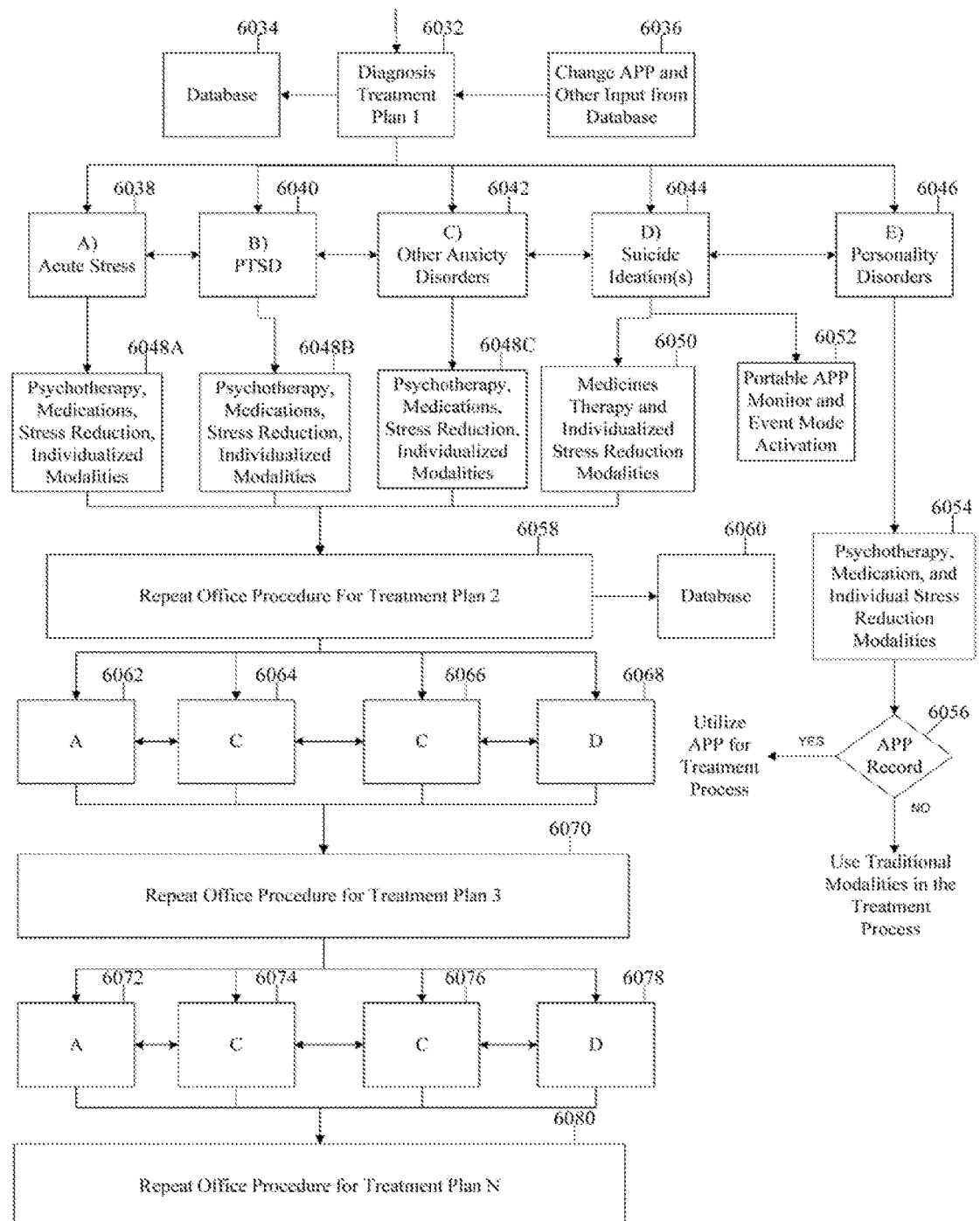

The relaxation modality chosen for the particular patient is also based on the severity of the patient's disorder. As shown in FIG. 6B, each of the anxiety disorder patients 5054, depression diagnosed patient 5068, and incomplete diagnosed patients are further subdivided into five progressively greater levels of severity, 5056-5064; 5070-5078; and 5084-5092, respectively. Once the baseline has been created, depending on the mood disorder (Anxiety Disorder Diagnosed Patients 5054, Depression Diagnosed Patients 5068, or Incomplete Diagnosed Patients 5082) treatment plan variants 5046, 5048, and 5050 will be used by the healthcare professional 5052,5066, and 5080. Based upon the severity levels, three different treatments 5094, 5102, and 5110 are used (FIG. 5C). These three treatment regimes include Psychotherapy 5096, 5104, and 5112; Medications 5098, 5106, and 5114; or a combination of both modalities 5100, 5108, and 5116.

During or after this therapy process, selective biometric behavioral monitoring modalities 5118, 6122, and 5126 can be used to administer and capture further data 5120, 5124, and 5128. This data can then be sent to the database 5132, 5136, and 5140. Depending on the results and any progress report of the patient's behavioral parameters 5130, 5134, and 5138, the healthcare professional can diagnose the degree of severity of the patient's disorder, and then place the patient in an appropriate treatment regimen 5142, 5144, and 5146. As shown in FIG. 5D, the patients are classified with respect to the type of disorder, such as anxiety 5148, 5156; depression 5150, 5170 or an incomplete diagnosis 5152, 5184.

The classification protocol employs inputs and diagnoses from physicians 5154, 5168, and 5182 and places the patient in an appropriate category based upon the severity of the patient's condition 5158-5166; 5172-5180; and 5186-5194 respectively. The classified patient is subjected to appropriate treatment regimes 5196, 5204, and 5212. The regimes include one or a combination of psychotherapy 5198, 5206, 5216; medication 5200, 5208, 5216; or some combination 5202, 5260, 5218 of medication and psychotherapy.

The next step is to select biometric behavioral modalities 5220, 5224, and 5228. Data is captured from the modalities at blocks 5227, 5226 and 5230, and transferred to the database 5234, 5238 and 5240. The database 5234, 5238 and 5240 and processor produce results and progress reports on the behavioral parameters 5232, 5236, and 5240. The reports 5232, 5236, and 5240 are then used to make appropriate diagnosis of the patient's condition 5246, 5248, and 5250. If the patient has not yet been "cured" or otherwise finished his treatment, the treatment can then be repeated as necessary until an appropriate end point is reached.

ii) Monitoring Evaluating and Treating the Mental Health of Military Personnel

Figure 7A:
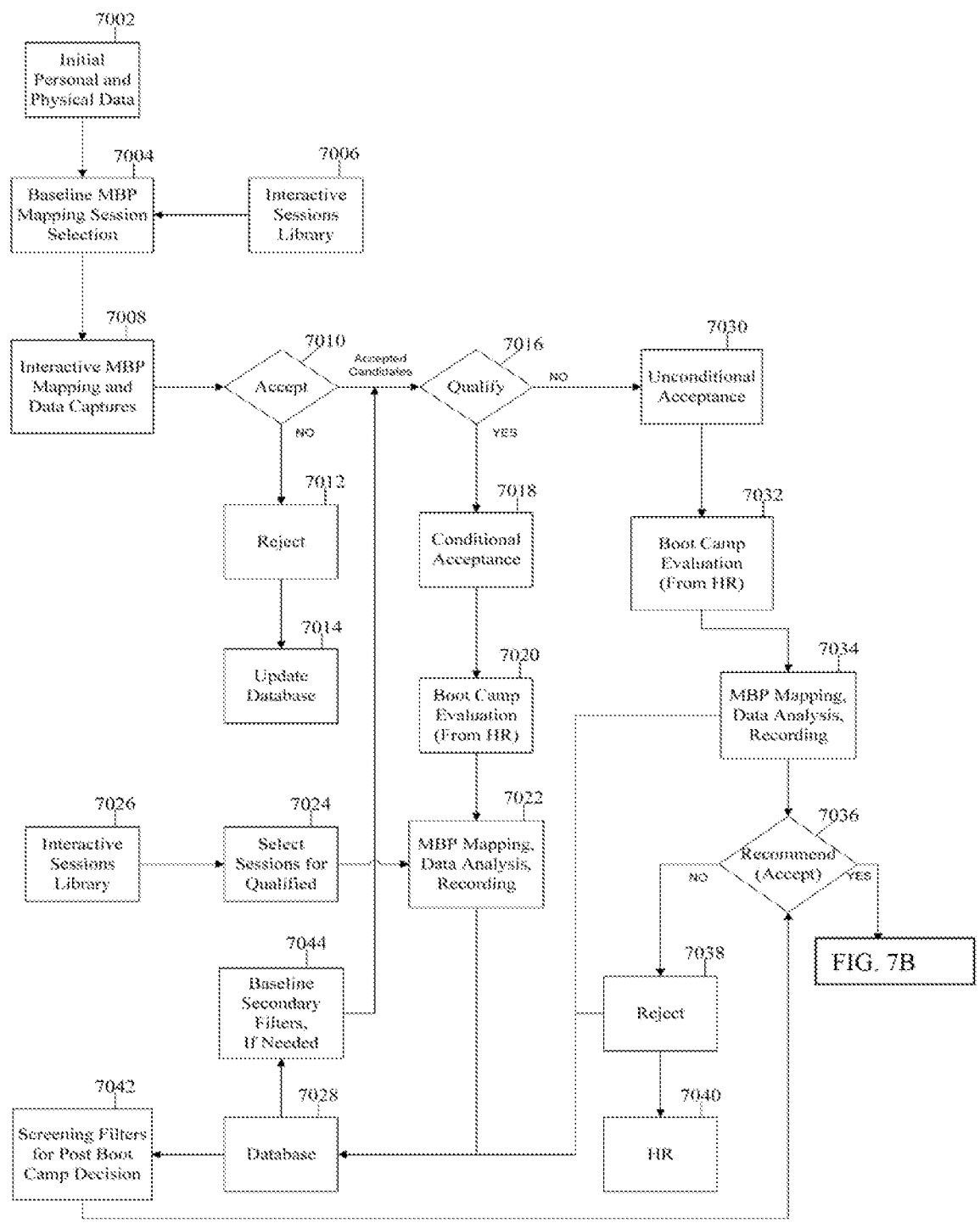
FIGS. 7A and 7B, when viewed together, comprise a block diagram depicting a system for tracking a patient's mental health in the beginning phase and throughout their career in high stress environments.
Figure 7B:
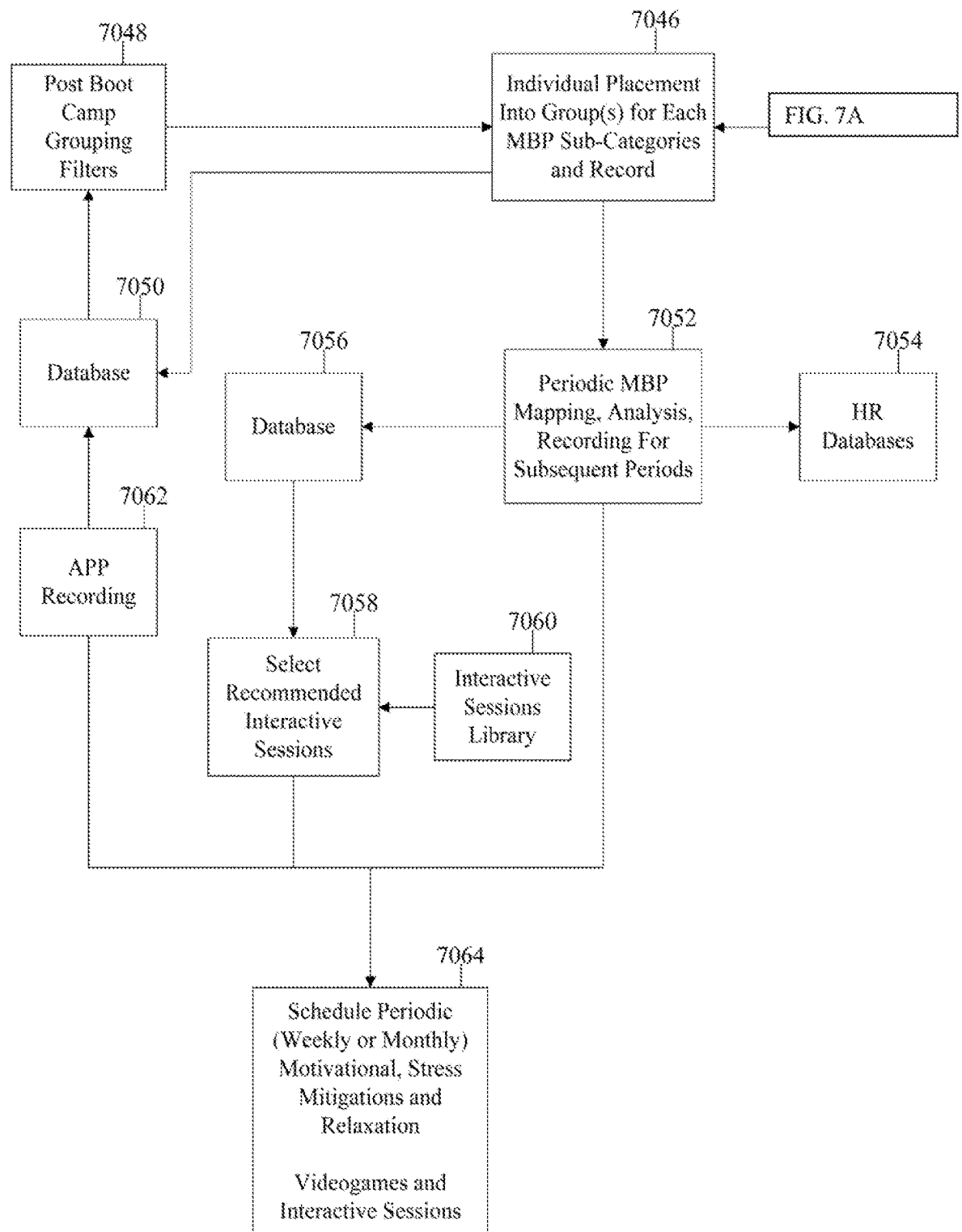

FIGS. 7A and 7B illustrates a system to track and monitor individuals in high stress environments. The system is applicable to many types of work situations and has particular utility in dealing with the military services personnel, who can be tracked and monitored from the beginning of their careers. This illustration describes an application to military services.

This two-part system utilizes an individual's motivation, behavior and performance mapping as a screening and decision tool in accepting candidates suitability to work in high stress situations such as military service. As an individual's first interaction when signing up for service, their initial personal and physical data 7002 is collected. A baseline motivation, behavior, and performance (MBP) mapping session 7004 is performed on the individual. The various components that are employed to stimulate the individual as per their personal background in the session are taken from a pre-existing library of interactive sessions 7006.

After the baseline MBP for the individual is created 7008, the system based upon current needs criteria of the employer, in this case the military, can make a recommendation that the employer either accept or reject 7010 the candidate. A recommendation is made based upon the characteristics exhibited by the candidate, including the system's measurement of parameters that are likely to be indicators of how the candidate will react to the long term and/or high degree of stress inherent to a military career.

If the candidate is rejected 7012, the database 7014 is updated to reflect any input about the candidate's MBP baseline so that the individual will be flagged if the candidate attempts to enlist at another recruiting office. If the candidate is accepted, the service personnel can evaluate whether the candidate is qualified 7016 for a conditional 7018 or unconditional acceptance 7030.

When the candidate is accepted conditionally, another series of MBP mapping, data analytics, and recording 7022 are conducted during boot camp or initial training programs by the concerned human resource departments 7020. The mapping and testing can be performed by employing appropriate testing session materials 7024 taken from the sessions contained within the Interactive Sessions Library 7026.

The second series of MBP mapping 7022 sends the results and data to the database 7028. Other screening filters and information useful for the post-boot camp decision 7042 are then processed. The second series of mapping results 8022 are then processed to create a report that helps in the determination of whether the conditionally accepted candidate should be rejected 7012 from the program or unconditionally accepted 7030; or otherwise remain in a conditionally accepted status.

These secondary questions 7042 can be optionally used for candidates after they have been accepted but not further qualified for either the conditional or unconditional acceptance. If the candidate has been unconditionally accepted, any further MBP mapping, data analytics or recording 7034 used during boot camp 7032, will be sent back to the database and can also be used for the candidate to be accepted into military service post-boot camp. If for any reason, the candidate has not met any standards set 7038, the candidate's information and any data analytics are sent to the database, and termination or separation is handled accordingly with the respective human resource departments 7042 of the military branch.

When the candidate is accepted post boot camp for selected services, the individual is placed into groupings for each MBP sub-categories that are specific to the individual 7046 (FIG. 7B) with any new results being sent to the database 7050. After the candidate has started working in high stress environments and the regular postings, the candidate (who is now a soldier) is given periodic MBP mapping and recording sessions 7052. Any further recommended interactive sessions 7058 selected from the database 7056 and their human resource files 7054, while using APP recording 7062 to test for changes during the soldier's careers is used to help the service branch monitor how the soldier is coping with the stress. This system of scheduling periodic motivational, stress, mitigation and relaxation modalities through various video games and interactive sessions 7064 is further illustrated in FIG. 8.

Figure 8A:
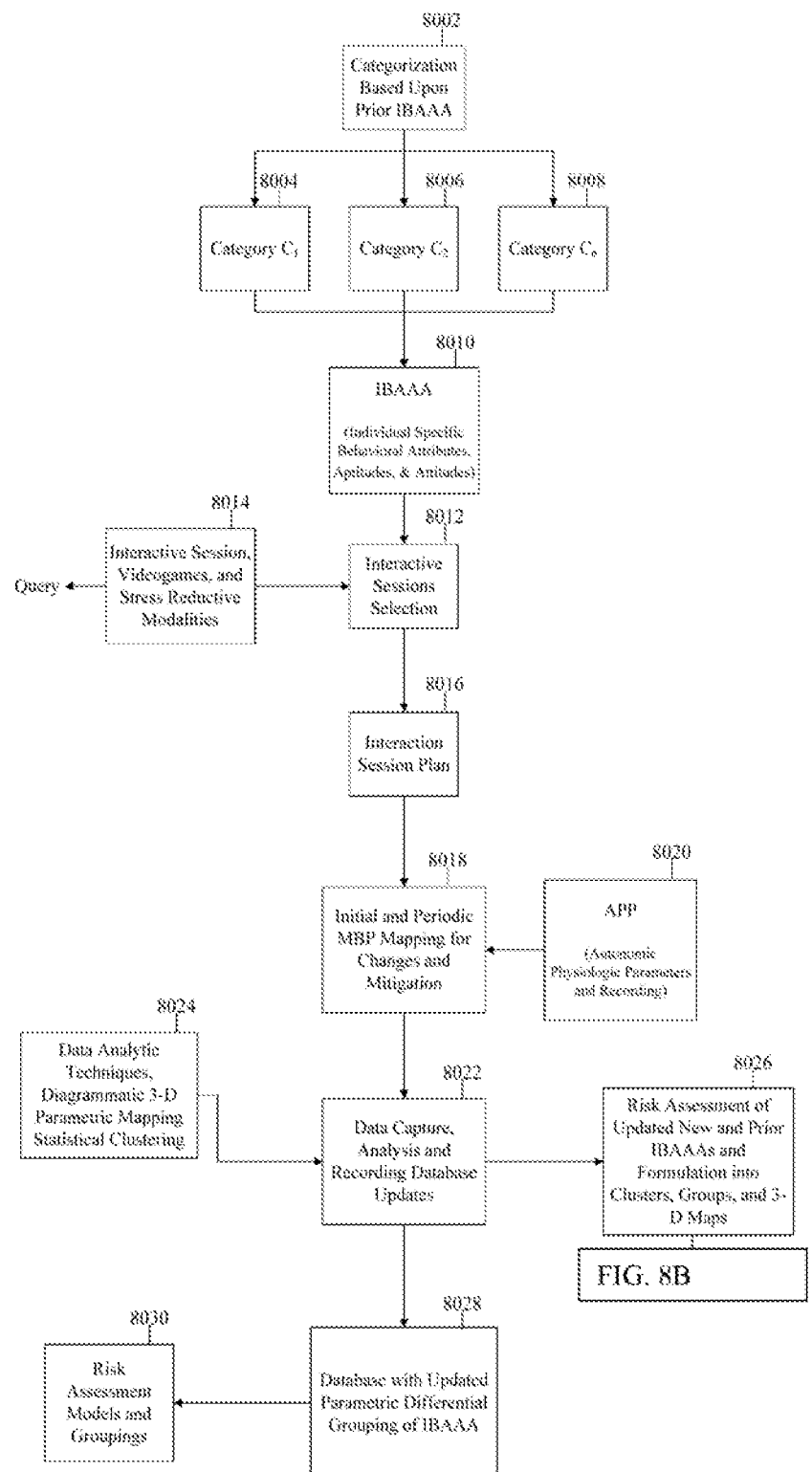
FIGS. 8A and 8B, when viewed together comprise a block diagram depicting a system for providing a mental health treatment regime for a patient in high stress environments.
Figure 8B:
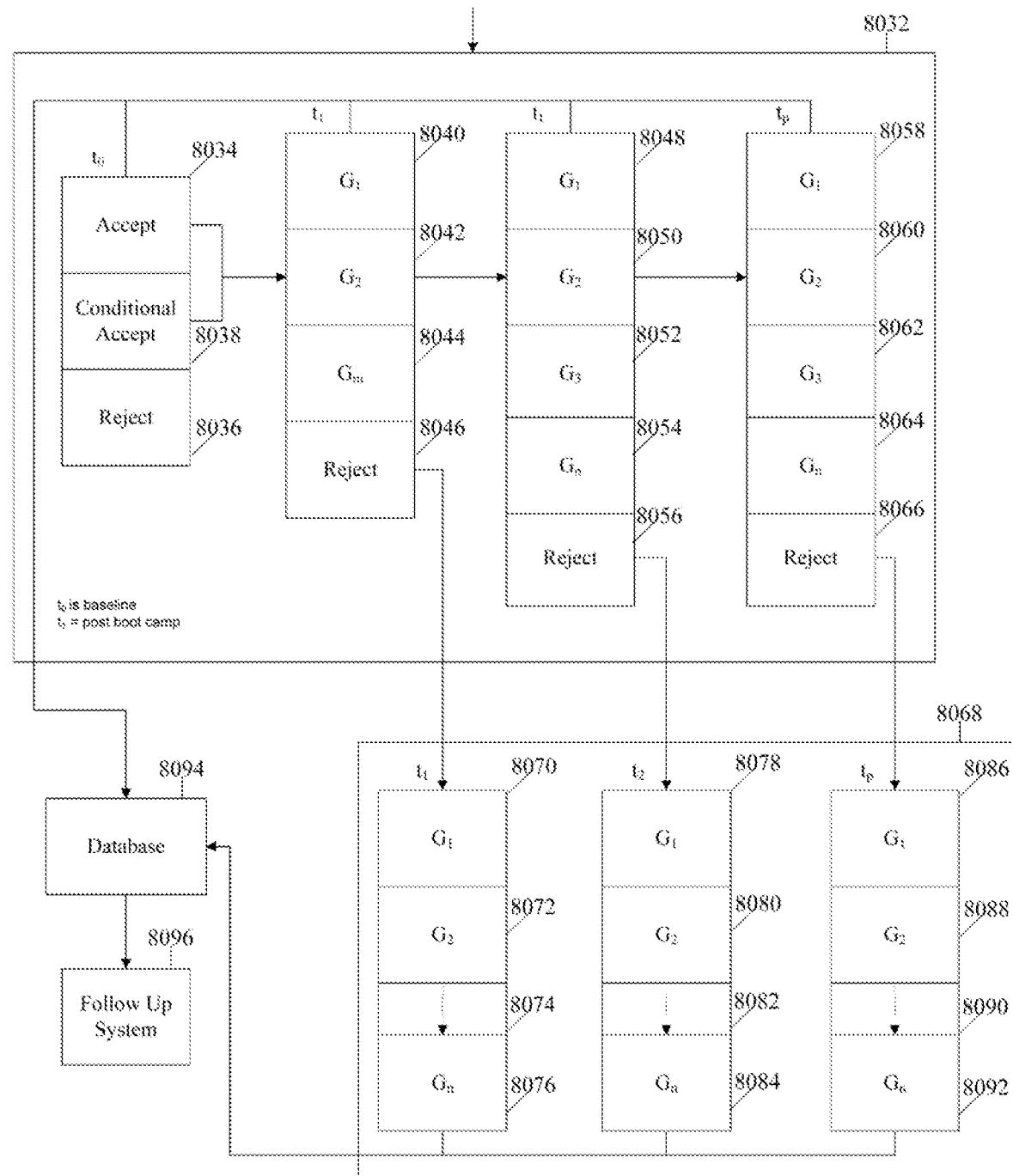

In FIG. 8, a system of using interactive sessions to treat individuals experiencing stress from working in high stress situations is illustrated. Based upon previous MBP mapping and recording sessions 8002, the individual is grouped into various categories. In the embodiment shown, three categories are employed including: Category $C_1$ 8004, Category $C_2$ 8006, and Category $C_n$ 8008. Depending upon the category 8004, 8006 or 8008 in which the soldier is placed, they will undergo testing across an exhaustive list of testing parameter to help determine the individual's specific behavioral attributes, attitudes and aptitudes (IBAAA) 8010. Examples of testing parameters include: family history; personal history (e.g., medical, abuse, education, hobbies, marital status, and likes and dislikes), personal journals; combat strain, habits, addictions; attitudes towards religious and spiritual beliefs; friends; and self-assessment on cognitive traits.

Based upon their categorization and IBAAA 8010, selection of an appropriate interaction session can be made from the library of sessions 8012 which include such things as:

video games and other stress reduction modalities 8014. The interactive session should be chosen to further the soldier's treatment by utilizing a database designed to discern, map, differentiate and mitigate the individual's mental condition based upon an interaction session plan 8016.

During this interaction session, the initial baseline and period MBP mapping and recording 8018 is conducted using APP monitoring 8020 to track any changes in the individual to assist in mitigating the mild stresses of general order. The data captured from the MBP mapping and recording 8022 is sent to the database. The information within the database 8028 is then processed to yield an updated parametric differential grouping based upon IBAAA 8010 and the database 8028 is updated. As shown in block 8026, further data analytic tools, techniques, diagrammatic mapping with statistical clustering analysis 8024 and risk assessment models can be employed to provide updated, more accurate, precise, and up-to-date information about the soldier 8030.

Subsequent to all data analytics and processing, a risk assessment metric, (validated on a prior sample population data) is used based upon all prior statistical analysis 8026 to design a treatment plan 8032 (FIG. 8B) for the soldier. Upon entry, the soldier is categorized into one of three categories: Accept 8034, Conditional Accept 8038, and Reject 8036 (which is setup as the baseline for the subject). The soldiers in the accept and conditional accept groupings will go through a sequence of treatment plans from $t_1, t_2, \ldots t_p$ as required and be categorized within those plans depending on their severity from $G_1$ 8040, $G_2$ 8042, ... to $G_n$ 8044 or a complete rejection 8046 out of the system for further treatment 8068.

Once the soldier is undergoing further treatment, the same system of categorization of the severity will be implemented with feedback from all testing being sent to the database 8094 and a further follow-up system 8096.

iii) Stress Diagnostics Mitigation System (SDMS) in High Stress Work Environment In another application of the present invention, a system is provided that tracks individuals who work in high stress environments. The system can track individuals from the beginning phase of their career by monitoring behavioral changes due to stress factors caused by the demands of the workplace alone, or in combination with non-work related stresses caused by (1) health issues, (2) family issues or (3) other adverse situations that impact the stress level of the particular employee. The intensity and/or consistency of stresses may have proportionately greater adverse impacts in certain members of the group. Often these more significantly impacted employees cannot be identified beforehand as being particularly susceptible to these stresses.

Existing tools and methodologies are used to intervene and help these individuals only when they are not functioning adequately; or exhibit stress related behavioral changes; or when co-workers or supervisors observe any changes; or when the employees voluntarily seek professional help. In many instances, this help may be provided too late to help the employee to recover completely. In the field of psychiatry, it is accepted that if an individual can be identified in the initial stages of adverse behavioral reactions, the mental disorders are less likely to progress into serious conditions and chronic disorders.

High stress work environments impact the mental health of employees at a much higher rate than those employed in non-high stress jobs. In many instances, due to the sensitive nature of the work performed in some of these high stress work environments, employees that are not able to perform at required standards may endanger team members, and cause significant collateral damages. It is important to observe and screen these employees for their physical, mental skills, and abilities to cope with severe stressful situations before they are placed in high stress work environments, which may further push them into severe adverse mental health disorders.

The present invention tracks employees working in high stress environments by testing them periodically, and/or after significant stress events or training programs to identify changes in the behavioral patterns of the employee. It utilizes the data set of behavioral factors, attributes, symptoms, and observable patterns that relate to an employee's focus, concentration, and/or attitude changes to help determine whether the employee is heading toward a path of a stress-related disorder.

The present invention also provides a system for identifying employees who do not seem to be affected or are impacted minimally by any of these stresses. The identification of such a non-effected group will help the organization in later phases to suitably place these employees in more demanding work environments where they are more likely to handle and cope with the higher stress levels of those jobs. The organization also can develop methodologies to identify and match the employees with the job demands, thereby improving their human resource management function for the long-term benefits like a resilient and productive work force with a low attrition rate.

Finally, the invention provides a system for tracking employees that exhibit a milder form of behavioral disorders or other early stage symptomatic ill effects by employing a series of interactive sessions involving desensitization objectives related to their general nature of work situations that may have triggered the initial anxiety or stress. The desensitization sessions can include: video games; faith-based group or individual sessions; fine arts related relaxation sessions; group exercises; yoga sessions; meditation; and counseling tailored to each individual's aptitudes and preferences.

iv) Catastrophe Induced Stress Diagnostics in Disaster Response Systems

In another application, the present invention provides a device and method to be quickly administered to large numbers of individuals affected by major catastrophes to help identify those persons traumatized by the event. These catastrophic events include all types of natural and man-made disasters such as hurricanes, tornados, tsunamis, earthquakes, terrorist attacks, wars, and nuclear or chemical accidents.

A particular individual's mental strength and stamina will influence the degree to which they will be prone to experience an emotional weakness after being exposed to gruesome scenes, the loss of life, property damages, and personal injury that occur during a catastrophe. A fraction of the people experiencing a catastrophic event can be affected deeply enough to experience serious mental disorders after the catastrophic event. A large segment of the population may experience a lesser degree of stress/trauma for a significant time period, such as months and years after the event. The stress and trauma can manifest itself as disturbed sleep patterns, different psychoses, and the inability to concentrate or focus properly in their work situations.

In this application of the present invention, technology called "Comparative Cognitive Methodology" (CCM) is employed to create a database of discriminant facial feature identifications similar to technologies developed by Carnegie Mellon University researchers generally, known as 'Facial Matching Using Soft-Biometric Attributes'. CCM is applied to different types of populations distinguished by their cultural, economic, gender, age, geographical region, and country distinctions. This database serves as a comparative and reference tool for future usage and deployment in a decentralized pattern in emergency shelters, as part of a special software toolset loaded into a portable digital device having wireless communication such as Wi-Fi or Bluetooth capabilities.

Subsequent to a catastrophic event occurrence, as the affected individuals enter emergency shelters, their facial moods are captured by the special camera located in every shelter as a data acquisition component feeding to the portable digital device as a part of a total system deployed as a part of Disaster Emergency Contingency Planning. This system is also enabled to communicate with handheld devices such as smart phones through password activation for the affected individuals to log on to and register their identities as a part of the database. This data is communicated to the central command center to assist in locating and identifying affected individuals immediately.

Informational videos can be downloaded by affected individuals and/or played on a common audio visual device like a Television or computer screen showing the aftermath of major disasters and how the disaster relief systems help affected individuals. In many instances, in relatively short times many affected individuals are given assistance. A number of actual similar disaster cases and the initial reactions, expectations, and resolutions of the issues (with the films of case studies and documented histories) are preloaded into the digital device box. This is the best source of information expected to reduce anxiety and stresses in a large segment of populations. It is documented that uncertainty and fear of unknown events, and the length of time this events may last, causes anxieties and stresses in a number of people. By viewing the most relevant scenarios of past incidences, the affected individuals are reassured and prepared to expect the next phase of the emergency relief systems actions.

Identification technology is applied to screen and identify deeply disturbed individuals from the at large populations, while they are converging into the emergency shelters for protection. These results are achieved by applying a mathematical algorithm that incorporates sequential identification via pattern recognition algorithms. These pattern recognition technologies perform the comparisons needed with a stored library of similar facial profiles, age, sex and racial backgrounds of populations exhibiting different moods under different phases of stresses, trauma by stage-wise filtering of noise, expected individual deviations, and matching muscular indicators in combinations. Once the specific individuals have been identified, a combination of desensitizing techniques and other known modalities can be employed to decompress, mitigate, or treat the stress/trauma.

The aptitudes and attributes of each individual are measured before tailored treatment modalities are administered, and to assist medical emergency personnel in identifying individuals that are least able to handle the stresses, and therefore are more likely to exhibit certain attributes leading to future mental sickness/traumas. This enables the medical personnel available at the site to triage their patients so that they can devote their time, efforts and treatment on those most in need or most likely to benefit from such services. This advantage of the invention to facilitate the prioritization of patients is especially useful in catastrophic events.

If a catastrophic event occurs, medical and professional personnel will likely be very thinly stretched due to disruptions in the logistical resources and services, while relatively greater numbers of individuals need these services. The processes and systems deployed by the present invention help to match the needy patients with the available scarce mental health care at the earliest instance.

The invention provides a computer-implemented system capable of administering pre-packaged desensitizing techniques that are targeted to particular groups of people rather than just individuals. These pre-packaged desensitizing techniques may include: group exercises; group games that include physical as well as computer-generated imagery; music therapy, faith based or inspirational sessions; inspirational and spiritual therapies; talks; and discourses. The techniques used for a particular group should be tailored to that group. For example, faith-based techniques would best be directed to persons having deeply held faith beliefs and convictions. The present invention is also able to identify these attributes; tailor the interactive modalities and sessions; and administer them very quickly (e.g., in a matter of days) to a very large population base.

The invention also provides a computer-implemented system employing the feedback from earlier sessions during the emergency to tailor the individual's subsequent medical care after the return of normalcy in the communities affected.

Figure 9A:
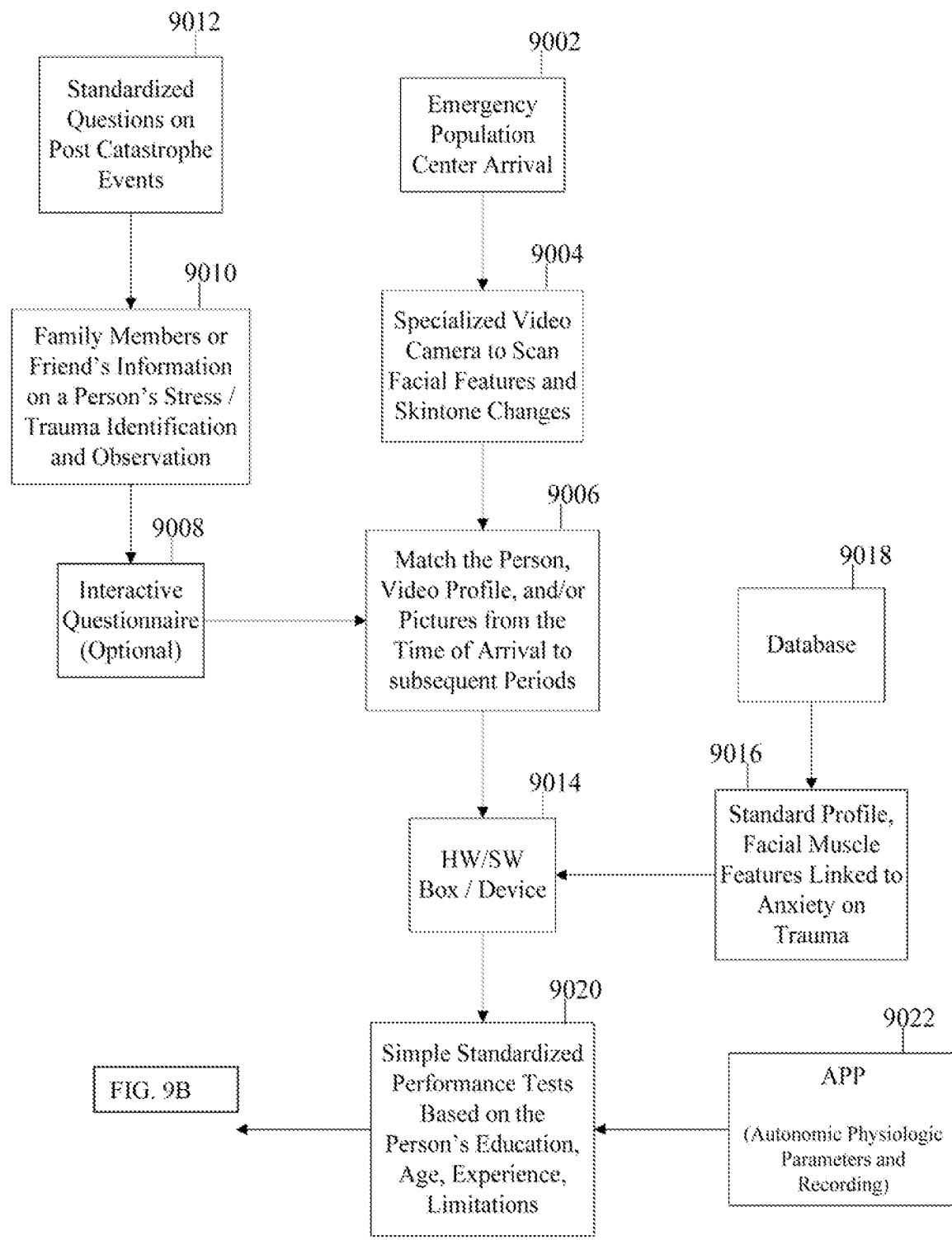
FIGS. 9A and 9B, when viewed together, comprise a block diagram depicting a system for providing a treatment regime for patients affected by major catastrophes.
Figure 9B:
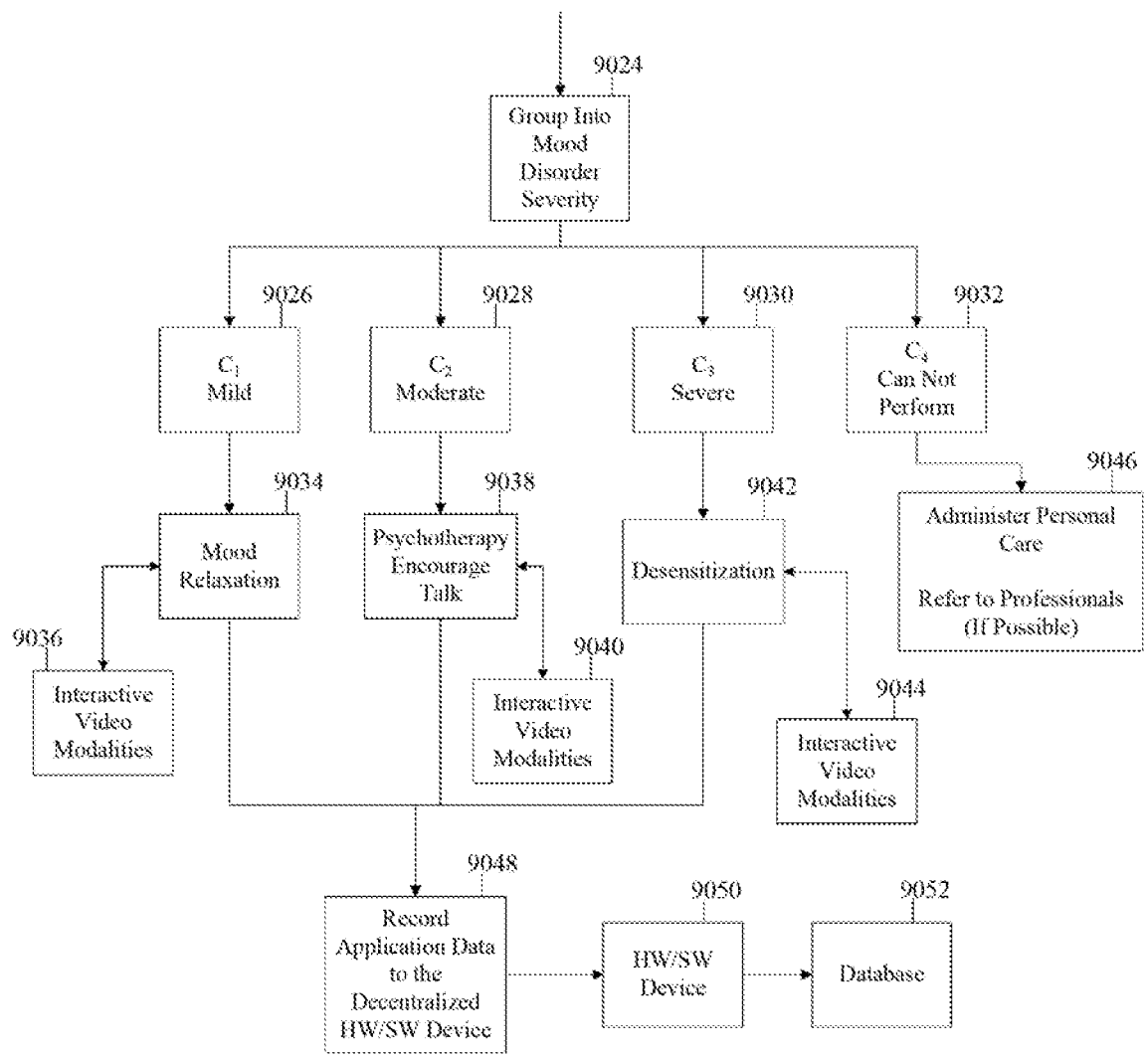

A more specific description of this application of the invention is depicted in the figures. In FIGS. 9A and 9B, a system of identifying and treating individuals experiencing mental disorders after major catastrophes is illustrated. After a major catastrophe has occurred, a portion of the population in the area affected will arrive at the emergency centers 9002. Once each individual has been identified at the emergency center, a specialized video camera will be used to scan facial features and/or any skin tone changes 9004. This video camera can also be used in any cataloging system used by the emergency center to identify individuals after major catastrophes. This video camera's documentation creates a unique individual profile to catalog pictures and/or video from the time of arrival until any subsequent periods there after 9006.

Subsequent to this video cataloging of the individual, a standardized questionnaire 9012 will be administered to all individuals, if feasible, at the emergency shelter. An optional questionnaire 9008 can be given to the individual to document any disturbing and strong emotions that may be developing after the initial shock. An additional system can be administered for any family member or friend that may identify a person's stress/trauma from various observations 9010. All this data and video records are then transferred to the batch processing hardware/software box or device 9014.

This hardware device can communicate, as the communications are restored, with the database 9018. The database 9018 can then remain a data acquisition mode, to continuously interact with the device to receive data and update the standardized profiles built to recognize any facial muscle features linked to anxieties or trauma 9016.

Once the hardware has cataloged all the individualized information, the database 9018 information is used to select the standardized performance tests 9020 that are most appropriate for the patient. The determination of which test is most appropriate is based upon factors such as the individual's educational background, age, gender, life experiences, and/or other limitations.

While these standardized performance tests are being conducted the APPs and recordings 9022 are used for the individuals being tested to group the individuals into the disorder severities 9024. In this example, four severity levels are used: $C_1$ Mild 9026, $C_2$ Moderate 9028, $C_3$ Severe 9030, or $C_4$ Can Not Perform 9032.

Once the individual has been placed into the appropriate category, various treatment modalities can be administered by the medical professionals. For individuals categorized under the $C_1$ or Mild Grouping, different types of mood relaxation modalities 9034, such as music therapy, faith exposure, yoga and meditation, and interactive video modalities 9036 can be used in batch or streaming mode.

For individuals in the $C_2$ or Moderate Grouping, medical professionals can use various psychotherapy modalities 9038 as well as a library of interactive video modalities 9040 available from the database. For individuals categorized under the $C_3$ or Severe grouping, various desensitization 9042 techniques are used in combination with various interactive video modalities 9044 from the database.

For individuals in the $C_4$ or Can Not Perform Grouping, the system will flag such individual, recommend professional care, and refer them to any available professionals 9046. During the treatment process, and upon completion for individuals in $C_1$, $C_2$, and $C_3$ groupings, the application data will be recorded to the decentralized hardware and software device 9048 that then sends the data to the database 9052.

As described above, the invention is unique in its ability to provide dynamic rather than static APP information captured from physiological reactions resulting from release and interactions of complex neuro-chemicals and hormones, historical memories, individual specific behavioral patterns coping mechanisms developed over the years, etc. While the APP changes and the observations are the outcomes of all the intermediary processes that are also studied by other techniques and tools used by practitioners and researchers, only this invention is capable of recording the dynamic APP changes resulting for the application of selected stimuli to relax and stimulate the patient during examination by a healthcare professional, wherein the interactive sessions can be tailored as per the individual's personal case history for inference.

We claim:

1. A method for behavioral and mental health testing in the psychiatry and clinical psychology fields to individually and periodically monitor changes in the emotional state of a subject that has a mental health disorder, the method comprising the steps of:
    selecting multiple stimuli from a plurality of stimuli categorized on the basis of different specific emotional reactions expected to be induced in the subject by each stimulus and a level of intensity of the stimulus, the selecting of the multiple stimuli being administered by a healthcare professional and the multiple stimuli being intentionally selected to induce at least one preselected specific emotional reaction of the specific emotional reactions for emotion mapping;
    conducting at least first and second sessions administered by a clinician during which the subject is in a controlled environment equipped with monitoring sensors, wherein each of the first and second sessions comprises individually exposing the subject to the multiple stimuli administered at least in part by computer while the subject is in the controlled environment and monitored with the monitoring sensors during each of the first and second sessions;
    during each of the first and second sessions, acquiring objective data with the monitoring sensors, wherein at least one of the objective data acquired with the monitoring sensors is a measured autonomic physiological parameter of the subject that is a reaction to the multiple stimuli during the first and second sessions and other of the objective data acquired with the monitoring sensors comprise one or more of speech, image, video, and audio data;
    transferring the objective data acquired during the first and second sessions to a database;
    processing, with statistical, mathematical, and scientific analytical tools, techniques, and algorithms performed by computer, the objective data to extract objective information from the autonomic physiological parameter about the subject's emotional state during each of the first and second sessions;
    comparing at least in part by computer the objective data acquired during the first and second sessions;
    inferring individual-specific behavioral and mental health changes in the emotional state of the subject by computing, with statistical, mathematical, and scientific analytical tools, techniques, and algorithms performed by computer, deviations of the objective data, including the autonomic physiological parameter, acquired during the first and second sessions, mapping the deviations by computer to create an emotion map, developing directions and dimensions of the deviations in the emotion map by computer, and grouping the individual-specific behavioral and mental health changes in the emotional state as a positive, neutral, or negative change relative to a baseline established with the objective data acquired during the first session; and
    presenting the objective data, the deviations, the emotion map, the individual-specific behavioral and mental health changes, and groupings of the individual-specific behavioral and mental health changes to a healthcare decision maker to categorize the directions and dimensions of the deviations of the individual-specific behavioral and mental health changes of the subject.

2. The method of claim 1, wherein the mental health disorder is an anxiety disorder, mood disorder, or depression.

3. The method of claim 1, wherein the mental health disorder is attention deficit hyperactivity disorder, autism spectrum disorder, bipolar disorder, borderline personality disorder eating disorder, or schizophrenia.

4. The method of claim 1, wherein the specific emotional reactions induced by the multiple stimuli are two or more of painful modes, mood relaxation, pleasant modes, and agitation modes.

5. The method of claim 4, wherein the multiple stimuli are selected from three categories: measurement sessions and metrics, calming and relaxation, and mitigate and desensitize.

6. The method of claim 5, wherein the multiple stimuli are presented through visual, oral, aural, kinesthetic, and/or written methods.

7. The method of claim 1, wherein each of the first and second sessions is a treatment, assessment, or tracking session administered by the clinician.

8. The method of claim 1, wherein the autonomic physiological parameter is selected from: blood pressure, pulse rate, respiratory rate, facial galvanic conductance, facial skin tone, changes in pupil size, pupil movement tracking, changes and frequency of eyelid fluttering, changes in sitting postures or bodily movements, unusual gestures or motions, movement of the leg or hand muscles, changes in voice pitch or tone, changes in facial muscles or expressions, brain electrical activity, skeletal muscle electrical activity and heart electrical activity.

9. The method of claim 1, wherein the database comprises: results of oral or written questionnaires; numerical data related to the autonomic physiological parameter; facial images; video clips; speech wave form data; and electrical activity data related to skin conductance, brain electrical activity, skeletal muscle activity, or heart electrical activity.

10. The method of claim 1, wherein the database comprises a computer network.

11. The method of claim 1, wherein the objective data comprises variety, volume, velocity and veracity of data that satisfies the definition of Big Data.

12. The method of claim 1, wherein the processing of the objective data comprises iterative processing until inferences from the autonomic physiological parameter are obtained.

13. The method of claim 1, wherein the processing of the objective data comprises, by computer, extracting sets of features from the objective data, processing the sets of features into clusters using clustering algorithms, and classifying the clusters into patterns using pattern classification algorithms to map the patterns onto the emotional state of the subject.

14. The method of claim 1, wherein the processing of the objective data comprises time cataloging the objective data with the multiple stimuli.

15. The method of claim 1, wherein the processing of the objective data comprises comparing the objective data acquired in each of the first and second sessions with corresponding objective data from other subjects within the database.

16. The method of claim 1, wherein the processing of the objective data comprises comparing the emotional state inferred from the first session with the emotional state inferred from the second session.

17. The method of claim 1, wherein the processing of the objective data comprises comparing the emotional state of the subject during each of the first and second sessions with corresponding emotional states of other subjects within the database.

18. The method of claim 1, wherein the processing of the objective data includes tracking the totality of the emotional state of the subject, the subject's dependent risk classifications and their changes from the first session to the second session.

19. The method of claim 18, wherein the subject's dependent risk classification includes classification of the subject into low, medium, or high risk treatment plan categories.

20. The method of claim 18, wherein the subject's dependent risk classification includes a classification of the stress severity level of the subject.

21. The method of claim 1, wherein the objective information is related to the subject's responses to the multiple stimuli.

22. The method of claim 21, wherein the first session is a baseline session.

23. The method of claim 21, further comprising categorizing the emotional state of the subject by comparing the objective data and the deviations of the subject to corresponding objective data and deviations of other subjects within the database.

24. The method of claim 21, wherein the objective information comprises an objective measurement of the subject's coping skills in responses to the multiple stimuli.

25. The method of claim 21, wherein the objective information comprises identified information sets related to malingerer cases.

26. The method of claim 21, wherein the objective information comprises an assessment of a progression of the mental health disorder of the subject in response to prescribed treatment plans.

27. The method of claim 21, wherein the objective information comprises identified sets of the autonomous physiological parameter related to tendencies of suicidal ideation, homicide, or other life-threatening activities.

28. The method of claim 1, wherein processing of the objective data comprises linking and integrating additional background information derived from the subject's mental health, physical health, or sleep records to infer changes in the emotional state.

29. The method of claim 1, wherein the processing of the objective data comprises comparing and developing inferences for changes in the autonomic physiological parameter and their relationship to specific disorders.

30. The method of claim 29, wherein the inferences comprise specific diagnostic markers for anxiety disorders, mood disorders, or depression.

31. The method of claim 30, wherein the markers may include integrating as necessary with additional sources of information such as family, social, and genetic information.

32. The method of claim 1, wherein the step of selecting the multiple stimuli is performed by a person and/or computer.

* * * * *